(12) United States Patent
Potyrailo et al.

(10) Patent No.: US 8,542,023 B2
(45) Date of Patent: Sep. 24, 2013

(54) HIGHLY SELECTIVE CHEMICAL AND BIOLOGICAL SENSORS

(75) Inventors: Radislav Alexandrovich Potyrailo, Niskayuna, NY (US); Cheryl Margaret Surman, Albany, NY (US); Andrew Arthur Paul Burns, Schenectady, NY (US); Nandini Nagraj, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 395 days.

(21) Appl. No.: 12/942,732

(22) Filed: Nov. 9, 2010

(65) Prior Publication Data

US 2012/0116683 A1 May 10, 2012

(51) Int. Cl.
*G01N 27/00* (2006.01)
(52) U.S. Cl.
USPC .......................................... 324/652; 324/71.1
(58) Field of Classification Search
USPC .......................................... 324/652, 670, 71.1
See application file for complete search history.

(56) References Cited

U.S. PATENT DOCUMENTS

| | | | | |
|---|---|---|---|---|
| 5,744,902 A | * | 4/1998 | Vig | 310/360 |
| 2005/0081374 A1 | * | 4/2005 | Eckstein et al. | 29/825 |
| 2007/0090926 A1 | | 4/2007 | Potyrailo et al. | |
| 2009/0278685 A1 | | 11/2009 | Potyrailo et al. | |

OTHER PUBLICATIONS

Radislav A. Potyrailo, et al.; Development of Radio-Frequency Identification Sensors Based on Organic Electronic Sensing Materials for Selective Detection of Toxic Vapors; 2009 American Institute of Physics.
Radislav A. Potyrailo, et al.; Selective Quantitation of Vapors and their Mixtures using Individual Passive Multivariable RFID Sensors; 2010; pp. 22-28.
Radislav A. Potyrailo, et al.;RFID Sensors based on Ubiquitous Passive 13.56-MHz RFID Tags and Complex Impedance Detection; 2008 John Wiley& Sons, Ltd.
EE Lim Tan, et al.; A Wireless, Passive Sensor for Quantifying Packaged Food Quality; Sep. 5, 2007; 1747-1756.

* cited by examiner

*Primary Examiner* — Vincent Q Nguyen
(74) *Attorney, Agent, or Firm* — Jean Testa; Fletcher Yoder

(57) ABSTRACT

Methods and sensors for selective fluid sensing are provided. Each sensor includes a resonant inductor-capacitor-resistor (LCR) sensor that is coated with a sensing material. In order to collect data, an impedance spectrum is acquired over a relatively narrow frequency range, such as the resonant frequency range of the LCR circuit. A multivariate signature may be calculated from the acquired spectrum to discern the presence of certain fluids and/or fluid mixtures. The presence of fluids is detected by measuring the changes in dielectric, dimensional, resistance, charge transfer, and other changes in the properties of the materials employed by observing the changes in the resonant electronic properties of the circuit. By using a mathematical procedure, such as principal components analysis (PCA) and others, multiple fluids and mixtures can be detected in the presence of one another, even in a high humidity environment or an environment wherein one or more fluids has a substantially higher concentration (e.g. 10×, 1,000,000×) compared to other components in the mixture.

40 Claims, 21 Drawing Sheets

| WATER VAPOR (PPM) | 1-OCTANOL DETECTION LIMIT (PPB) | WATER VAPOR OVERLOAD |
| --- | --- | --- |
| 0 | 33 | 0 |
| 2807 | 30 | 92,312 |
| 5614 | 31 | 183,546 |
| 11,228 | 36 | 312,423 |
| 16,842 | 56 | 299,092 |

68

| WATER VAPOR (PPM) | 1-NONANOL DETECTION LIMIT (PPB) | WATER VAPOR OVERLOAD |
| --- | --- | --- |
| 0 | 6 | 0 |
| 2807 | 6 | 454,348 |
| 5614 | 6 | 961,512 |
| 11,228 | 7 | 1,594,127 |
| 16,842 | 9 | 1,918,104 |

HIGHLY SELECTIVE CHEMICAL AND BIOLOGICAL SENSORS

STATEMENT REGARDING FEDERALLY SPONSORED RESEARCH & DEVELOPMENT

This invention was made with Government support and funded in part by the National Institute of Environmental Health Sciences under Grant No. 1R01ES016569-01A1 and funded in part by the Air Force Research Laboratory under Contract No. FS8650-08-C-6869. The Government has certain rights in the invention.

BACKGROUND

The subject matter disclosed herein relates to chemical and biological sensors, and more particularly, to highly selective chemical and biological sensors.

Chemical and biological sensors are often employed in a number of applications were the detection of various vapors maybe used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications such as residential home monitoring, home land security in airports in different environmental and clinical settings and other public venues wherein detection of certain harmful and/or toxic vapors may be particularly useful.

One technique for sensing such environmental changes is by employing a sensor, such as an RFID sensor, coated with a particular sensing material. Also, sensors maybe arranged in an array of individual transducers which are coated with sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In certain applications multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response, complicates fabrication of the array.

Further, in many practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors.

Various embodiments disclosed herein may address one or more of the challenges set forth above.

BRIEF DESCRIPTION

In accordance with one embodiment, there is provided a sensor comprising a resonant inductor-capacitor-resistor (LCR) circuit and a sensing material disposed over the LCR circuit. The sensing material is configured to allow selective detection of at least six different analyte fluids or gases from an analyzed fluid or gas mixture.

In accordance with another embodiment, there is provided a method of detecting analytes in a fluid. The method comprises acquiring an impedance spectrum over a resonant frequency range of a resonant sensor circuit. The method further comprises calculating a multivariate signature from the acquired impedance spectrum.

In accordance with another embodiment, there is provided a method of detecting chemical or biological species in a fluid. The method comprises measuring a real part and an imaginary part of an impedance spectrum of a resonant sensor antenna coated with a sensing material. The method further comprises calculating at least six spectral parameters of the resonant sensor antenna coated with the sensing material. The method further comprises reducing the impedance spectrum to a single data point using multivariate analysis to selectively identify an analyte. The method further comprises determining one or more environmental parameters from the impedance spectrum.

In accordance with another embodiment, there is provided a sensor comprising a transducer and a sensing material disposed on the transducer. The transducer has a multivariate output to independently detect effects of different environmental parameters on the sensor. The sensing material has a preserved magnitude of response to an analyte over a broad concentration range of an interferent.

In accordance with another embodiment, there is provided a method for controlling selectivity of a sensor response of a sensor having an integrated circuit (IC) chip. The method comprises powering the IC chip to at least one power level to affect an impedance spectral profile of the sensor. The method further comprises collecting spectral parameters of the sensor response at the at least one power level. The method further comprises performing multivariate analysis of the spectral parameters. The method further comprises calculating values of environmental parameters to which the sensor is exposed from data produced by performing the multivariate analysis and using stored calibration coefficients.

In accordance with another embodiment, there is provided a method for controlling selectivity of a sensor response of an LCR sensor having a sensing material disposed thereon. The method comprises powering an inductor-resistor-capacitor (LCR) sensor to at least two power levels to affect at least one of the dipole moment, the dielectric constant, and the temperature of the sensing material. The method further comprises collecting spectral parameters of the sensor response at the at least two power levels. The method further comprises performing multivariate analysis of the spectral parameters from combined impedance spectral profiles of the LCR sensor at the different power levels. The method further comprises calculating values of environmental parameters to which the LCR sensor is exposed from data produced by performing the multivariate analysis.

DRAWINGS

These and other features, aspects, and advantages of the present invention will become better understood when the following detailed description is read with reference to the accompanying drawings in which like characters represent like parts throughout the drawings, wherein:

FIG. 11 illustrates tables relating to the comparative plots of FIG. 10, in accordance with embodiments of the invention;

DETAILED DESCRIPTION

Figure 1:
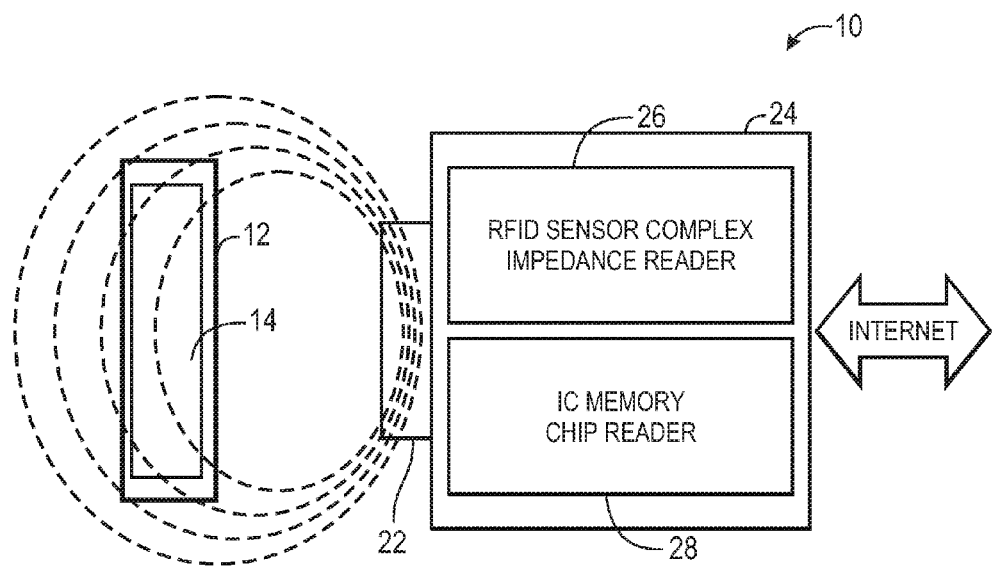
FIG. 1 illustrates a sensing system, in accordance with embodiments of the invention.

Embodiments disclosed herein provide methods and systems for selective vapor sensing wherein a single sensor is provided and is capable of detecting multiple vapors and/or mixtures of vapors alone, or in the presence of one another. The disclosed sensors are capable of detecting different vapors and mixtures even in a high humidity environment or an environment wherein one or more vapors has a substantially higher concentration (e.g. 10×) compared to other components in the mixture. Each sensor includes a resonant inductor-capacitor-resistor (LCR) sensor that is coated with a sensing material. Nonlimiting examples of LCR sensors include RFID sensors with an integrated circuit (IC) memory chip, RFID sensors with an IC chip, and RFID sensors without an IC memory chip (chipless RFID sensors). LCR sensors can be wireless or wired. In order to collect data, an impedance spectrum is acquired over a relatively narrow frequency range, such as the resonant frequency range of the LCR circuit. The technique further includes calculating the multivariate signature from the acquired spectrum and manipulating the data to discern the presence of certain vapors and/or vapor mixtures. The presence of vapors is detected by measuring the changes in dielectric, dimensional, charge transfer, and other changes in the properties of the materials employed by observing the changes in the resonant electronic properties of the circuit. By using a mathematical procedure, such as principal component analysis (PCA) and others, multiple vapors and mixtures can be detected in the presence of one another and in the presence of an interferent as further described below. Embodiments disclosed herein provide methods and systems for selective fluid sensing wherein a single sensor is provided and is capable of detecting multiple fluids and/or mixtures of fluids alone, or in the presence of one another.

To more clearly and concisely describe the subject matter of the claimed invention, the following definitions are provided for specific terms, which are used in the following description and the appended claims.

The term "fluids" includes gases, vapors, liquids, and solids.

The term "digital ID" includes all data stored in a memory chip of the RFID sensor. Nonlimiting examples of this data are manufacturer identification, electronic pedigree data, user data, and calibration data for the sensor.

The term "monitoring process" includes, but is not limited to, measuring physical changes that occur around the sensor. For example, monitoring processes including monitoring changes in a chemical, automotive, biopharmaceutical, food or beverage manufacturing process related to changes in physical, chemical, and/or biological properties of an environment around the sensor. Monitoring processes may also include those industry processes that monitor physical changes as well as changes in a component's composition or position. Nonlimiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.) Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady-state measurements of individual vapors and their mixtures.

The term "environmental parameters" is used to refer to measurable environmental variables within or surrounding a manufacturing or monitoring system. The measurable environmental variables comprise at least one of physical, chemical and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "analyte" includes any desired measured environmental parameter.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors". The appropriate selection of features is performed from all potential features that can be calculated from spectra. Multivariable spectral parameters are described in U.S. patent application Ser. No. 12/118,950 entitled "Methods and systems for calibration of RFID sensors", which is incorporated herein by reference.

The term "resonance impedance" or "impedance" refers to measured sensor frequency response around the resonance of the sensor from which the sensor "spectral parameters" are extracted.

The term "protecting material" includes, but is not limited to, materials on the LCR or RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another non-limiting example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper, polymeric, and inorganic films such as polyesters, polypropylene, polyethylene, polyethers, polycarbonate, polyethylene terepthalate, zeolites, metal-organic frameworks, and cavitands. The protecting material can be arranged between the transducer and sensing film to protect the transducer. The protecting material can be arranged on top of the sensing film which is itself is on top of the transducer to protect the sensing film and transducer. The protecting material on top of the sensing film which is itself is on top of the transducer can serve to as a filter material to protect the sensing film from exposure to gaseous or ionic interferences. Nonlimiting examples of filter materials include zeolites, metal-organic frameworks, and cavitands.

As used herein the term "sensing materials and sensing films" includes, but is not limited to, materials deposited onto a transducer's electronics module, such as LCR circuit components, an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the LCR or RFID sensor, the impedance sensor response changes as a function of pH. Thus, such an LCR or RFID sensor works as a pH sensor. When such a polyaniline film is deposited onto the LCR or RFID sensor for detection in gas phase, the impedance sensor response also changes upon exposure to basic (for example, $NH_3$) or acidic (for example HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaking into the liquid environment, the sensing materials are attached to the sensor surface using standard techniques, such as covalent bonding, electrostatic bonding and other standard techniques known to those of ordinary skill in the art.

The terms "transducer and sensor" are used to refer to electronic devices such as RFID devices intended for sensing. "Transducer" is a device before it is coated with a sensing or protecting film or before it is calibrated for sensing application. "Sensor" is a device typically after it is coated with a sensing or protecting film and after being calibrated for sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where a specific RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the complex impedance response, resonance peak position, peak width, peak height and peak symmetry of the impedance response of the sensor antenna, magnitude of the real part of the impedance, resonant frequency of the imaginary part of the impedance, antiresonant frequency of the imaginary part of the impedance, zero-reactance frequency, phase angle, and magnitude of impedance, and others as described in the definition of the term sensor "spectral parameters". The "RFID sensor" can have an integrated circuit (IC) memory chip attached to antenna or can have no IC memory chip. An RFID sensor without an IC memory chip is an LCR sensor. An LCR sensor is comprised of known components such as at least one inductor (L), at least one capacitor (C), and at least one resistor (R) to form an LCR circuit.

The term "single-use container" includes, but is not limited to, manufacturing or monitoring equipment, and packaging, which may be disposed of after use or reconditioned for reuse. Single-use packaging in the food industry includes but is not limited to food and drinks packaging, candy and confection boxes. Single-use monitoring components include, but are not limited to, single-use cartridges, dosimeters, and collectors. Single use manufacturing containers include, but are not limited to, single-use vessels, bags, chambers, tubing, connectors, and columns.

The term "writer/reader" includes, but is not limited to, a combination of devices to write and read data into the memory of the memory chip and to read impedance of the antenna. Another term for "writer/reader" is "interrogator".

In accordance with embodiments disclosed herein, an LCR or an RFID sensor for sensing vapors, vapor mixtures, fluids, fluid mixtures and biological species is described. As previously described, the RFID sensor includes an RFID tag coated with a sensing material. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through an antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements.

In one embodiment a passive RFID tag with or without an IC memory chip may be employed. Advantageously, a passive RFID tag does not rely on a battery for operation. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with a writer/reader that operates at 13.56 MHz while the sensor portion of the RFID tag operates from 5 to 20 MHz.

Depositing sensing films onto passive RFID tags creates RFID chemical, biological, or physical sensors. RFID sensing is performed by measuring changes in the RFID sensor's impedance as a function of physical changes around the sensor, as described further below. Examples of physical changes include, but are not limited to, temperature, pressure, conductivity, and dielectric properties. If the frequency response of the antenna coil, after deposition of the sensing film, does not exceed the frequency range of operation of the tag, the information stored in the microchip can be identified with a conventional RFID writer/reader. Similarly, an impedance analyzer (sensor reader) can read the impedance of the antenna coil to correlate the changes in impedance to the chemical and biological species of interest and to physical, chemical, or/and biological changes of environmental parameters around the sensor.

In operation, after coating of the RFID tag with a chemically sensitive film, both the digital tag ID and the impedance of the tag antenna may be measured. The measured digital ID provides information about the identity of the tag itself, such as an object onto which this tag is attached, and the properties of the sensor (e.g. calibration curves for different conditions, manufacturing parameters, expiration date, etc.). For multicomponent detection, multiple properties from the measured real and imaginary portions of the impedance of a single RFID sensor may be determined, as described further below.

In alternate embodiments, the selective sensor performance can be achieved not only by using a sensing material deposited onto the transducer, but also by depositing a protective film onto the transducer, or using the bare transducer itself.

In accordance with the embodiments described herein, in order to achieve high selectivity detection of analytes in the presence of high levels of interferences, the sensor should exhibit a number of characteristics. First, the selected transducer should include a multivariate output to independently detect the effects of different environmental parameters on the sensor. Second, the sensing material should have a preserved magnitude of response to an analyte over a wide concentration range of an interferent. The response to the relatively small analyte concentrations should not be fully suppressed by the presence of the relatively high concentrations of the interferents. Third, the response of the sensing material to interference species is allowed and may exist but should not compete with the response to the analyte and should be in a different direction of the multivariate output response of the transducer.

To achieve these characteristics, in one embodiment, the sensing material has multiple response mechanisms to fluids where these response mechanisms are related to the changes of dielectric constant, resistance, and swelling of the sensing material where these changes are not fully correlated with each other and produce different patterns upon exposure to individual vapors and their mixtures. Further, the LCR transducer can have multiple components of LCR response from the LCR circuit where these multiple components of LCR response originate from the different factors affecting the transducer circuit with the nonlimiting examples that include material resistance and capacitance, contact resistance and capacitance between the transducer and sensing material, resistance and capacitance between the transducer substrate and sensing material. Further, the LCR transducer can have multiple conditions of LCR circuit operation where an integrated circuit chip is a part of the sensor circuit.

Thus, one method for controlling the selectivity of the sensor response involves powering of the integrated circuit chip to affect the impedance spectral profile. The different impedance spectral profiles change the selectivity of sensor response upon interactions with different fluids. The IC chip or IC memory chip on the resonant antenna contains a rectifier diode and it can be powered at different power levels to influence the impedance spectral profile of the sensor. The differences in spectral profiles at different power levels are pronounced in different values of Fp, F1, F2, Fz, Zp, Z1, Z2, and calculated values of C and R. In one embodiment, the enhanced sensor selectivity is achieved through the appropriate selection of at least one power level of the IC chip or IC memory chip operation. In another embodiment, the enhanced sensor selectivity is achieved through the appropriate selection of at least two power levels of the IC chip or IC memory chip operation and analyzing the combined impedance spectral profiles of the sensor under different power levels. Powering of the sensor with at least two power levels is performed in the alternating fashion between a relatively low and relatively high power. The alternating powering of the sensor with at least two power levels is performed on the time scale which is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences.

Another method of controlling the selectivity of the sensor response involves applying different powers to the LCR or to RFID sensor to affect the dipole moment, the dielectric constant, and/or temperature of the material in proximity to the sensor. The material in proximity to the sensor refers to the sensing material deposited onto the sensor and/or the fluid under investigation. These changes in the dipole moment, the dielectric constant, and/or temperature of the material in proximity to the sensor when exposed to different power levels of LCR or RFID sensor operation originate from the interactions of the electromagnetic field with these materials. Powering of the sensor with at least two power levels is performed in the alternating fashion between a relatively low and relatively high power. The alternating powering of the sensor with at least two power levels is performed on the time scale which is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences. Operation at a selected power or at multiple powers results in selective detection of fluids with the same dielectric constant.

Figure 2:
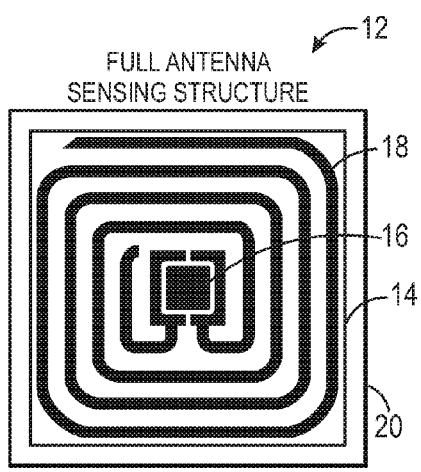
FIG. 2 illustrates an RFID sensor, in accordance with embodiments of the invention.

Turning now to the figures and referring initially to FIG. 1, a sensing system 10 is provided to illustrate the principle of selective vapor sensing utilizing an RFID sensor 12 having a sensing material 14, coated thereon. Referring briefly to FIG. 2, the sensor 12 is a resonant circuit that includes an inductor-capacitor-resistor structure (LCR) coated with the sensing material 14. The sensing material 14 is applied onto the sensing region between the electrodes, which form sensor antenna 18 that constitute the resonant circuit. As will be described further below, by applying the sensing material 14 onto the resonant circuit, the impedance response of the circuit will be altered. The sensor 12 may be a wired sensor or a wireless sensor. The sensor 12 may also include a memory chip 16 coupled to resonant antenna 18 that is coupled to a substrate 20. The memory chip 16 may include manufacturing, user, calibration and/or other data stored thereon. The memory chip 16 is an integrated circuit device and it includes RF signal modulation circuitry fabricated using a complementary metal-oxide semiconductor (CMOS) process and a nonvolatile memory. The RF signal modulation circuitry components include a diode rectifier, a power supply voltage control, a modulator, a demodulator, a clock generator, and other components.

Figure 3:
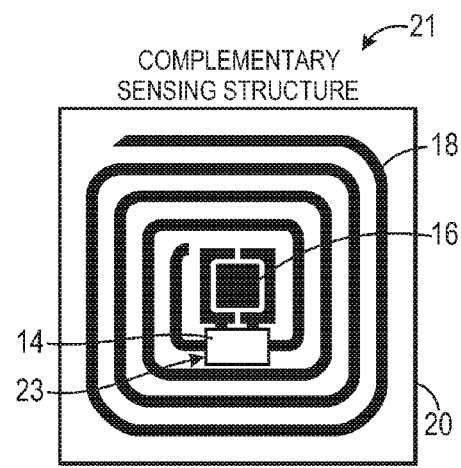
FIG. 3 illustrates an RFID sensor, in accordance with alternate embodiments of the invention.

FIG. 3 illustrates an alternative embodiment of the sensor 12, designated by reference numeral 21, wherein a complementary sensor 23 comprising a sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Nonlimiting examples of complementary sensors are interdigitated sensors, resistive sensors, and capacitive sensors. Complementary sensors are described in U.S. patent application Ser. No. 12/118,950 entitled "Methods and systems for calibration of RFID sensors", which is incorporated herein by reference.

In one embodiment, a 13.56 MHz RFID tag may be employed. During operation of the sensing system 10, the impedance Z(f) of the sensor antenna 18 and the digital sensor calibration parameters stored on the memory chip 16 may be acquired. Referring again to FIGS. 2 and 3, measurement of the resonance impedance Z(f) of the antenna 18 and the reading/writing of digital data from the memory chip 16 are performed via mutual inductance coupling between the RFID sensor antenna 18 and the pickup coil 22 of a reader 24. As illustrated, the reader 24 may include an RFID sensor impedance reader 26 and an integrated circuit memory chip reader 28. The interaction between the RFID sensor 12 and the pickup coil 22 can be described using a general mutual inductance coupling circuit model. The model includes an intrinsic impedance $Z_C$ of the pickup coil 22 and an intrinsic impedance $Z_S$ of the sensor 12. The mutual inductance coupling M and the intrinsic impedances $Z_C$ and $Z_S$ are related through the total measured impedance $Z_T$ across the terminal of the pickup coil 22, as represented by the following equation:

$$Z_T = Z_C + (\omega^2 M^2 / Z_S), \qquad (1)$$

wherein ω is the radian carrier frequency and M is the mutual inductance coupling coefficient.

Sensing is performed via monitoring of the changes in the properties of the sensing material 14 as probed by the electromagnetic field generated in the antenna 18 (FIG. 2). Upon reading the RFID sensor 12 with the pickup coil 22, the electromagnetic field generated in the sensor antenna 18 extends out from the plane of the sensor 12 and is affected by the dielectric property of an ambient environment providing the opportunity for measurements of physical, chemical, and biological parameters. For measurements of highly conducting species (liquids or solids), the protecting or sensing material 14 provides a protective barrier that separates the conducting medium from the resonant antenna. For measurement in highly conducting media, the protecting or sensing material 14 prevents the RFID tag from direct contact with the liquid and loss of the sensor resonance. For measurements of low conducting media (e.g., approximately 0.5 µS/cm), the sensor can operate and perform measurements without a protecting material.

Similarly, sensing is performed via monitoring of the changes in the properties of the sensing material 14 as probed by the electromagnetic field generated in the complementary sensor 23 (FIG. 3). Upon reading the RFID sensor 21 with the pickup coil 22, the electromagnetic field generated in the complementary sensor 23 extends out from the plane of the complementary sensor 23 and is affected by the dielectric property of an ambient environment providing the opportunity for measurements of physical, chemical, and biological parameters. For measurements of highly conducting species (liquids or solids), the protecting or sensing material 14 provides a protective barrier that separates the conducting medium from the resonant antenna. For measurement in highly conducting media, the protecting or sensing material 14 prevents the RFID tag from direct contact with the liquid and loss of the sensor resonance. For measurements of low conducting media, the sensor can operate and perform measurements without a protecting material.

Figure 4:
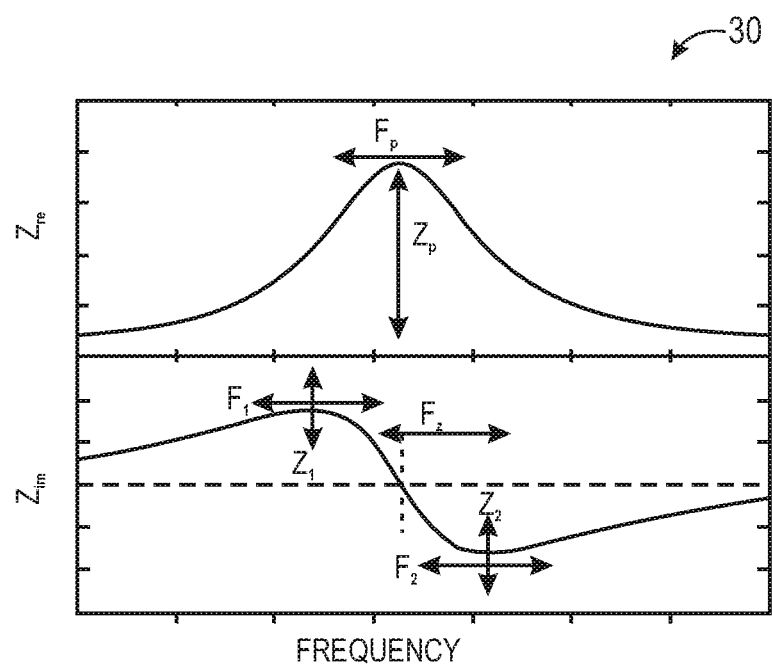
FIG. 4 illustrates measured responses of an RFID sensor, in accordance with embodiments of the invention.

FIG. 4 illustrates an example of measured responses of an exemplary RFID sensors 12 and 21, in accordance with embodiments of the invention, which includes the sensor's full impedance spectra and several individually measured spectral parameters. To selectively detect several vapors or fluids using a single RFID sensor, such as the RFID sensors 12 and 21, the real $Z_{re}(f)$ and imaginary $Z_{im}(f)$ parts of the impedance spectra $Z(f)=Zre(f)+jZ_{im}(f)$ are measured from the sensors 12 and 21 coated with a sensing material and at least four spectral parameters are calculated from the measured $Z_{re}(f)$ and $Z_{im}(f)$, as illustrated in the plot 30 of FIG. 4. Seven spectral parameters can be calculated as illustrated in the plot 30 of FIG. 4. These parameters include the frequency position Fp and magnitude Zp of $Z_{re}(f)$, the resonant F1 and anti-resonant F2 frequencies of $Z_{im}(f)$, the impedance magnitudes Z1 and Z2 at F1 and F2 frequencies, respectively, and the zero-reactance frequency FZ. Additional parameters, such as quality factor may also be calculated. From the measured parameters, resistance R, capacitance C, and other parameters of the sensors 12 and 21 can be also determined. Multivariate analysis may be used to reduce the dimensionality of the impedance response, either from the measured real $Z_{re}(f)$ and imaginary $Z_{im}(f)$ parts of the impedance spectra or from the calculated parameters Fp, Zp, F1 and F2, and possibly other parameters to a single data point in multidimensional space for selective quantization of different vapors or fluids, as will be appreciated by those skilled in the art, and as will be described further below.

The presence of even relatively low levels of interferences (0.1-10 fold overloading levels) represents a significant limitation for individual sensors due to their insufficient selectivity. This problem can be addressed with an introduction of a concept of sensor arrays. Unfortunately, in practical situations (e.g. urban, environmental, and workplace monitoring, breath analysis, and others), sensor arrays suffer from interference effects at high ($10^2$-$10^6$ fold) overloading levels. These interference effects reduce the use of both, sensors and sensor arrays. Advantageously, embodiments described herein provide techniques to overcome these two key scientific limitations of existing sensors and sensor arrays, such as difficulty or inability of operating with high overloading from interferences and of selective measurements of multiple vapors and their mixtures using a single sensor.

The well-accepted limitations of impedance spectroscopy in practical sensors for trace analyte detection include relatively low sensitivity and prohibitively long acquisition times over the broad frequency range. Embodiments described herein enhance the ability to measure changes in properties of the sensing material by putting the material onto the electrodes of the resonant LCR sensor circuit. Similarly, the disclosed embodiments enhance the ability to measure changes in properties of the fluid in proximity to the electrodes of the resonant LCR sensor circuit. Experimental testing examined the effects of changing dielectric constant on sensing electrodes both with and without a resonator. Compared to the conventional impedance spectroscopy, the bare resonant LCR sensor provided an at least 100-fold enhancement in the signal-to-noise (SNR) over the smallest measured range of the dielectric constant difference ($\Delta\in$) with the corresponding improvement of detection limit of dielectric constant determinations.

Performance of the LCR sensor as analyzed using multivariate analysis tools provides an advantage of improved selectivity over the processing of individual responses of individual sensors. In particular, test results indicate the relations between Fp and Zp and the relations between calculated sensor resistance R and calculated sensor capacitance C have a much less selectivity between responses to different vapors or fluids as compared to the relations between multivariable parameters such as PC1 and PC2 and others. Further, the LCR sensors demonstrate independent contact resistance and contact capacitance responses that improve the overall selectivity of the multivariable response of the LCR sensors. This selectivity improvement originates from the independent contributions of the contact resistance and contact capacitance responses to the equivalent circuit response of the sensor.

Diverse sensing materials may be advantageously utilized on the sensing region of the LCR resonant sensor because analyte-induced changes in the sensing material film affect the impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor.

Sensing films for the disclosed LCR and RFID sensors may include a variety of materials provided the environmental changes are detectable by changes in resonant LCR circuit parameters. Non-limiting examples of possible sensing film materials are a hydrogel such as poly(2-hydroxyethyl methacrylate), a sulfonated polymer such as Nafion, an adhesive polymer such as silicone adhesive, an inorganic film such as sol-gel film, a biological-containing film such as DNA, antibody, peptide or other biomolecules deposited as a film, a biological-containing film such as DNA, antibody, enzyme, peptide, polysaccharide, protein, aptamer, or other biomolecules or viruses, spores, cells, deposited as a part of a inorganic or polymeric film, a composite film, a nanocomposite film, functionalized carbon nanotube film, or film made of surface functionalized gold nanoparticles, electrospun polymeric, inorganic, and composite nanofibers, and nanoparticles that have one dielectric property and incorporated in a matrix that have another dielectric property.

Sensing materials can be selected to have different dielectric constants ranging from about 2 to about 40. Nonlimiting examples include polyisobutylene (PIB, $\in'_r$=2.1), ethyl cellulose (EC, $\in'_r$=3.4), polyepichlorihydrin (PECH, $\in'_r$=7.4), cyanopropyl methyl phenylmethyl silicone (OV-225, $\in'_r$=11), dicyanoallyl silicone (OV-275, $\in'_r$=33). The use of these materials provides the ability to tailor the relative direction of sensing response upon exposure to vapors of different dielectric constant. The different partition coefficients of vapors into these or other sensing materials further modulate the diversity and relative direction of the response.

"Composites" are materials made from two or more constituent materials with significantly different physical or chemical properties, which remain separate and distinct on a macroscopic level within the finished structure. Nonlimiting examples of composites include carbon black composites with poly(4-vinylphenol), poly(styrene-co-allyl alcohol), poly(vinyl chloride-covinyl acetate), and other materials. "Nanocomposites" are materials made from two or more constituent materials with significantly different physical or chemical properties, which remain separate and distinct on a nanoscale level within the finished structure. Nonlimiting examples of nanocomposites include: carbon nanotube nanocomposites with polymers (such as poly(N-vinylpyrrolidone), polycarbonate, polystyrene, etc.); semiconducting nanocrystal quantum dot nanocomposites with polymers, metal oxide nanowires, and carbon nanotubes; metal nanoparticles or nanoclusters functionalized with carbon nanotubes.

Sensing materials exhibit analyte responses which can be described by one or more of three response mechanisms of LCR or RFID sensors such as resistance changes, dielectric constant changes and swelling changes. A composite sensing material can be constructed which incorporate multiple different individual sensing materials which each respond to analytes by predominantly different response mechanisms. Such composite sensing material produces an enhanced diversity in the multivariate response. Such composite sensing materials may be homogeneously or inhomogeneously mixed or locally patterned over specific portions of the LCR resonator.

For example, a wide range of metal oxide semiconductor materials (e.g. ZnO, $TiO_2$, $SrTiO_3$, $LaFeO_3$, etc) exhibit changes in resistance upon exposure to analyte gases, but some mixed metal oxides (e.g. CuO—$BaTiO_3$, ZnO—$WO_3$) change their permittivity/capacitance upon exposure to analyte vapors. By combining these materials either as mixtures, or by spatially separated deposition onto the same sensor, their separate contributions to the local environment surrounding the sensor are used to enhance the diversity of response mechanisms for a single analyte, thus enhancing selectivity.

As a further example, ligand-coated conducting (e.g. metal) nanoparticles are used as vapor and fluid sensing materials because of their strong changes in resistance due to localized swelling induced by analyte adsorption into the ligand shell and the subsequent change in tunneling efficiency between neighboring conducting nanoparticles and dielectric constant changes of the environment between these conducting nanoparticles. In combination with a dielectric polymer (nonlimiting examples include silicones, poly(etherurethane), polyisobutylene siloxane fluoroalcohol, etc.), conjugated polymer (polyaniline, polythiophene, poly(vinyl ferrocene), poly(fluorene)-diphenylpropane), poly(3,4-ethylenedioxythiophene) polypyrrole, bilypyrrole) or any other material (nonlimiting examples include porphyrins, metalloporphyrins, metallophthalocyanines, carbon nanotubes, semiconducting nanocrystals, metal oxide nanowires) that responds to analyte adsorption with more pronounced changes in capacitance or resistance, a sensor with a wider range of analyte responses is developed.

Further, in order to avoid potentially deleterious effects of disparate materials on each other in a composite sensing material (e.g. high dielectric constant medium suppressing conduction in a conductive filler material), this material components are chosen to locally phase separate due to hydrophylic/hydrophobic interactions or mutual immiscibility, allowing the different mechanisms active in each component to be sensed by the sensor. In another embodiment, a composite sensing material can be formed as sectors of individual materials deposited adjacent to each other onto a single sensor. In another embodiment, a composite sensing material can be formed as layers of individual materials deposited on top of each other onto a single sensor.

In certain embodiments, sensing materials may be porphyrins, metalloporphyrins, metallophthalocyanines, and related macrocycles. In these materials, gas sensing is accomplished either by π-stacking of the gas into organized layers of the flat macrocycles or by gas coordination to the metal center without the cavity inclusion. Metalloporphyrins provide several mechanisms of gas response including hydrogen bonding, polarization, polarity interactions, metal center coordination interactions and molecular arrangements. Molecules of porphyrins, metalloporphyrins, metallophthalocyanines, and related macrocycles can be also assembled into nano structures.

Further types of materials include aligned nanostructures where alignment is performed by various known methods (dielectrophoretic alignment, alignment during material polymerization, alignment due to spatial confinement, alignment during slow solvent evaporation, and others), self-assembled structures such as colloidal crystal structures of the same size of particles, multilayers of colloidal crystal films where different layers have different size of assembled particles, nanoparticle assemblies where the particles have core-shell structure with the particle core of one dielectric property and particle shell of another dielectric property, bio-inspired materials, zero-dimensional nanomaterials, one-dimensional nanomaterials, two-dimensional nanomaterials, and three-dimensional nanomaterials.

Self-assembled structures include colloidal crystal structures of the same size of particles, multilayers of colloidal crystal films where different layers have different sizes of assembled particles, nanoparticle assemblies where the particles have core-shell structure with the particle core of one dielectric property and particle shell of another dielectric property. Nonlimiting examples of materials of self-assembled colloidal crystal structures include polystyrene, polymethylmethacrylate, polyvinyltoluene, styrene/butadiene copolymers, styrene/vinyltoluene copolymers, and silica. The typical diameters of these colloidal particles depend on the type of material and may range from 50 nanometers to 25 micrometers. Nonlimiting examples of colloidal crystal structures with multiple layers include at least one layer of particles of one size assembled as a colloidal array onto the sensor substrate and at least one layer of particles of another size assembled as a colloidal array on top of the previous layer. Nonlimiting examples of bio-inspired materials include super hydrophobic or superhydrophilic materials.

Nonlimiting examples of zero-dimensional nanomaterials include metal nanoparticles, dielectric nanoparticles, core-shell nanoparticles, and semiconducting nanocrystals. Nonlimiting examples of one-dimensional nanomaterials include nanotubes, nanowires, nanorods, and nanofibers. Nonlimiting examples of two-dimensional nanomaterials include graphene. Nonlimiting examples of three-dimensional nanomaterials include self assembled films of several layers of colloidal spheres.

Nonlimiting examples of nanoparticles that have core-shell structure with the particle core of one dielectric property and particle shell of another dielectric property include: metal (gold, silver, their alloy, etc.) core nanoparticles and organic shell layers (dodecanethiol, decanethiol, 1-butanethiol, 2-ethylhexanethiol, hexanethiol, tert-dodecanethiol, 4-methoxy-toluenethiol, 2-mercaptobenzoxazole, 11-mercapto-1-undecanol, 6-hydroxyhexanethiol); polymeric core (polystyrene, polymethylmethacrylate) and inorganic shell (silica); isolating core (polystyrene, polymethylmethacrylate, silica) and semiconducting shell (carbon nanotubes, TiO2, ZnO, SnO2, WO3), and carbon nanotube core that is decorated with metal nanoparticles. The nanoparticles of metal (gold, silver, their alloy, etc.) core nanoparticles and organic shell layers can be further modified with organic and polymeric molecules. Nonlimiting example of organic molecules include porphyrins, metalloporphyrins, metallophthalocyanines, and macrocycles, cavitands, supramolecular compounds. Nonlimiting example of polymeric molecules include polymeric molecules with different dielectric constants ranging from 2 to 40. Nonlimiting examples include polyisobutylene (PIB, $\in'_r=2.1$), ethyl cellulose (EC, $\in'_r=3.4$), polyepichlorihydrin (PECH, $\in'_r=7.4$), cyanopropyl methyl phenylmethyl silicone (OV-225, $\in'_r=11$), dicyanoallyl silicone (OV-275, $\in'_r=33$). A nonlimiting example of fabrication of these sensing materials involves (1) preparation of metal core nanoparticles with an organic shell in a solvent, (2) mixing this composition with another composition of polymeric or organic molecules in a solvent, and (3) depositing a sensing film on an LCR or RFID transducer from this combined mixture. The use of these materials in combination with metal core nanoparticles provides the ability to tailor the relative direction of sensing response upon exposure to vapors of different dielectric constant. The different partition coefficients of vapors into these or other sensing materials further modulate the diversity and relative direction of the response.

Other sensing materials include semiconducting metal oxides, zeolites, cavitands, ionic liquids, liquid crystals, crown ethers, enzymes, polysilsesquioxanes, metal-organic frameworks (MOFs).

Other sensing materials include synthetic dielectric and conducting polymers with different polymer side group functionalities, and different polymer formulations; biomolecules for gas-phase sensing; cavitands with dominating intracavity complexation and a totally suppressed non specific extracavity adsorption of vapors provided by cavitand deposition; porphyrins and related molecules as individual molecules and as assembled into polymers and nanostructures.

To further improve selectivity of response, overcoating of sensing films with auxiliary membrane filter films may be performed. Nonlimiting examples of these filter films include zeolite, metal-organic framework, and cavitand filters.

These diverse sensing materials shown as nonlimiting examples are provided on the sensing region of the LCR or RFID resonant sensor because analyte-induced changes in the sensing material film affect the complex impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor, as illustrated further below, with regard to EXPERIMENTAL DATA.

Experimental Data

Resonant antenna structures, such as those described above, were used for demonstration of the disclosed techniques. Various sensing materials were applied onto the resonant antennas by conventional draw-coating, drop coating, and spraying processes. Measurements of the impedance of the RFID and LCR sensors were performed for example with a network analyzer (Model E5062A, Agilent Technologies, Inc. Santa Clara, Calif.) under computer control using LabVIEW. The network analyzer was used to scan the frequencies over the range of interest (i.e., the resonant frequency range of the LCR circuit) and to collect the impedance response from the RFID and LCR sensors.

For gas sensing, different concentrations of vapors were generated using an in-house built computer-controlled vapor-generation system. Collected impedance data was analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

Example 1

Selective Detection of Six Vapors with a Single Sensor

Figure 5:
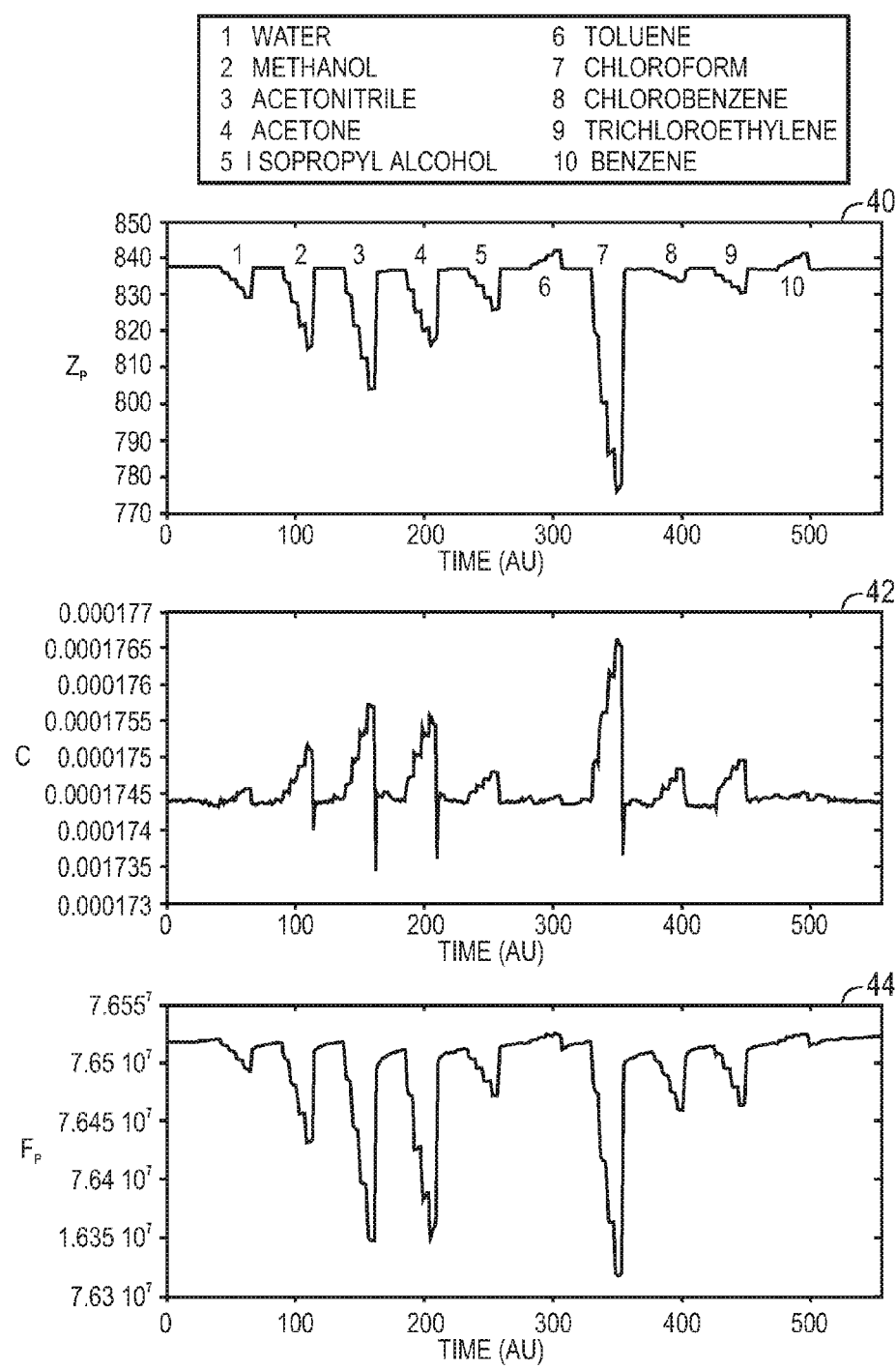
FIGS. 5 and 6 illustrate test data demonstrating an RFID sensor capable of detecting six different vapors, in accordance with embodiments of the invention.
Figure 6:
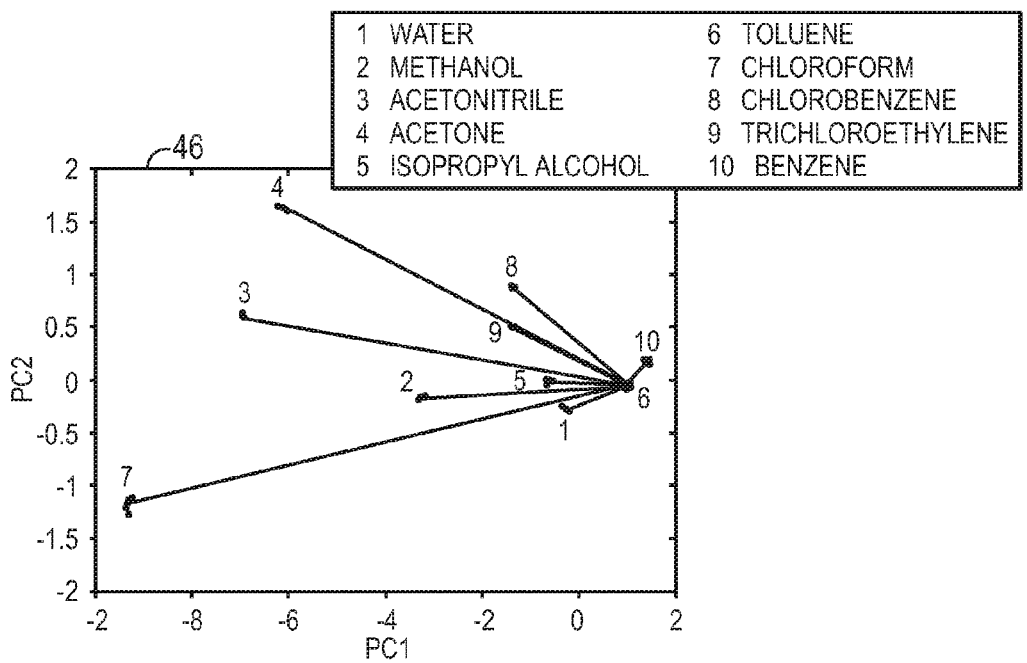

As illustrated in FIGS. 5 and 6, test results were obtained to demonstrate the selective detection of six different vapors, using a single sensor, such as the sensor 12 described above. As illustrated in FIG. 5, the sensor was exposed to the following 10 vapors over a period of time:

| 1 | water |
| 2 | methanol |
| 3 | acetonitrile |
| 4 | acetone |
| 5 | isopropyl alcohol |
| 6 | toluene |
| 7 | chloroform |
| 8 | chlorobenzene |
| 9 | trichloroethylene |
| 10 | benzene |

The sensing material used to coat the RFID tag was carefully chosen and provided the ability to selectively detect at least six of the listed vapors. In the present experiment, the chosen sensing material was poly(etherurethane) (PEUT) dissolved in a nonpolar solvent such as dichloromethane. During the experiment, the RFID sensor was incrementally exposed to 10 vapors over a period of time. The test was conducted in steps, where the concentration of each respective vapor was increased with each step. By monitoring changes in certain properties and examining various responses over time and at increasing concentration levels, the data demonstrated the ability to distinguish six of the 10 vapors tested in the above-described experiment.

For instance, the frequency position Fp and magnitude Zp of the real part of the total resistance $Z_{re}(f)$, as well as the capacitance C, are illustrated in FIG. 5, as response plots 44, 40 and 42, respectively. The tests for each vapor were conducted and plotted over 4 increments of increasing concentration, as clearly indicated by the stepped nature of the response for each vapor. For example, referring to the plot of the magnitude Zp, the magnitude Zp for each vapor (1-10) exhibits four steps, correlative to the increases in concentration of each vapor over time. From examining this plot alone, certain of the vapors can clearly be distinguished from one another. By way of example, the magnitude Zp response for chloroform (7) is very strong, and it notably discernable from each of the other responses. Accordingly, the exemplary RFID sensor is able to selectively detect chloroform (7). In contrast, when viewing the magnitude Zp response of methanol (2), it appears very similar to the magnitude Zp of acetone (4). Based solely on the magnitude Zp response, the exemplary RFID sensor may not be suitable for detecting and distinguishing between these two vapors.

However, as previously described, a number of other responses (e.g. the frequency position Fp and the capacitance C) may also be analyzed and may provide further information that may be manipulated and analyzed in order to provide a way to distinguish vapors, wherein one particular response may not be sufficient. Referring to the test data for frequency position Fp response plot 44, the frequency position Fp of methanol (2) is distinguishable from the frequency position Fp of acetone (4). Accordingly, the exemplary RFID sensor may be sufficient for distinguishing such vapors, when other responses, such as the frequency position Fp (as opposed to the magnitude Zp response alone), are analyzed.

One convenient way of analyzing various responses of the sensor is to use principal components analysis (PCA) to produce a multivariate signature. As will be appreciated, PCA analysis is a mathematical process, known to those skilled in the art, that is used to reduce multidimensional data sets to lower dimensions for analysis. For instance, the various responses for each vapor at a given concentration may be reduced to a single data point, and from this, a single response for each vapor which may be represented as a vector, may be discerned, as illustrated in FIG. 6. FIG. 6 represents a PCA plot 46 of the various responses of the 10 vapors described with reference to FIG. 5. As will be appreciated, PC1 represents the response with the most variation, while PC2 represents the response with the next most variation. As illustrated, the vectors for acetone (4) and trichloroethylene (9) may be difficult to distinguish from one another. Similarly, the vectors for toluene (6) and benzene (10) may be difficult to distinguish from one another. However, the remaining six vapors are clearly distinguishable from one another. Accordingly, the instant test data provides support for a sensor capable of discerning between at least six vapors, here water (1), methanol (2), acetonitrile (3), isopropyl alcohol (5), chloroform (7), and chlorobenzene (8).

In addition, vapor mixtures may also be discernable from the PCA plot. For instance, one may be able to extrapolate a vector plot of a mixture of acetonitrile (3) and chloroform (7). Such additional extrapolated data may also be used to selectively detect mixtures of selected vapors. Further, by varying the selected sensing material, even greater numbers of selective vapor detection has been demonstrated, utilizing a single RFID sensor.

Example 2

Selective Detection of Eight Vapors with a Single Sensor

Figure 7:
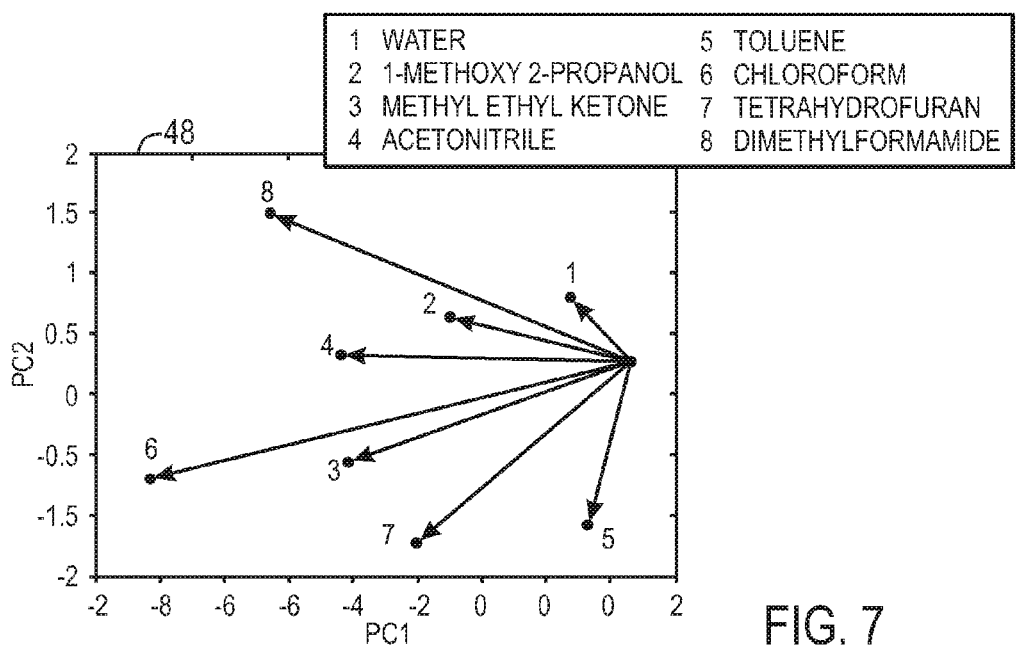
FIG. 7 illustrates test data demonstrating an RFID sensor capable of detecting eight different vapors, in accordance with embodiments of the invention.

As illustrated in FIG. 7, test results were obtained to demonstrate the selective detection of eight different vapors, using a single sensor, such as the sensor 12 described above. The sensing material used to coat the RFID tag was carefully chosen and provided the ability to selectively detect the listed vapors. In the present experiment, the chosen sensing material was PEUT dissolved in a nonpolar solvent such as dichloromethane. As previously described, the tests were conducted with incremental increases in concentration. As illustrated in the plot 48 of FIG. 7, the sensor coated with PEUT was able to discriminate the following 8 vapors:

| 1 | water |
| 2 | 1-methoxy 2-propanol |
| 3 | methyl ethyl ketone |
| 4 | acetonitrile |
| 5 | toluene |
| 6 | chloroform |
| 7 | tetrahydrofuran |
| 8 | dimethylformamide |

Example 3

Selective Detection of Binary and Ternary Mixtures with a Single Sensor

Figure 8:
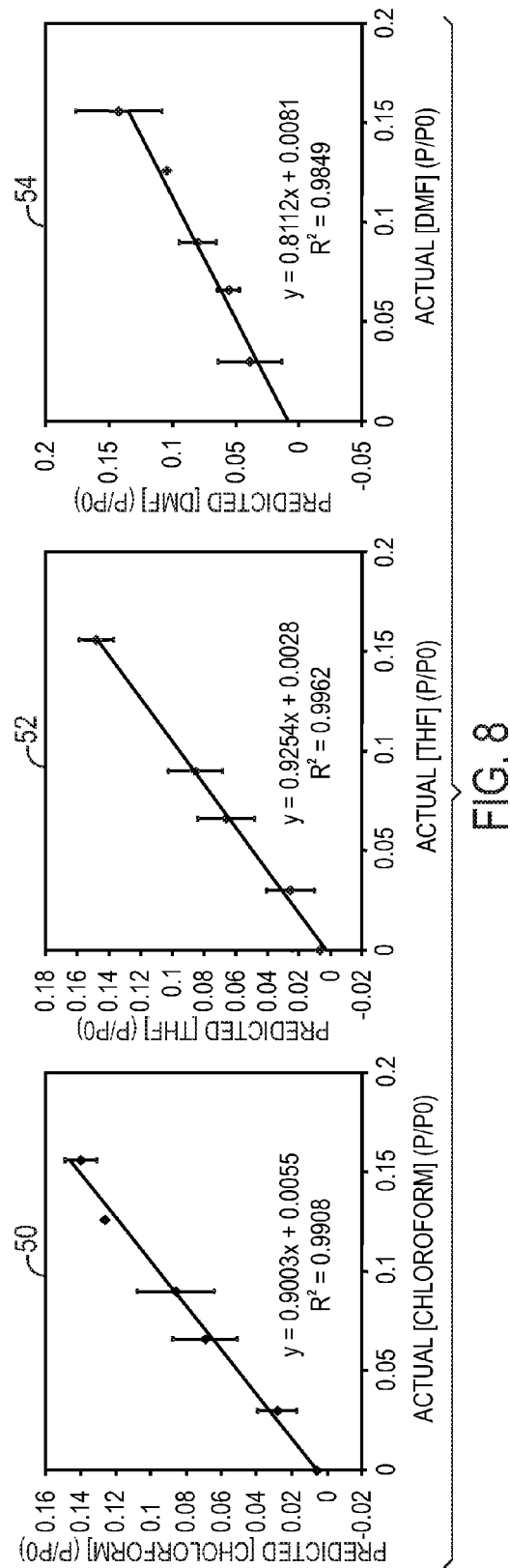
FIG. 8 illustrates test data demonstrating a single sensor capable of determining concentrations of individual vapors in their binary and ternary mixtures, in accordance with embodiments of the invention.

Vapors chloroform, tetrahydrofuran (THF), and dimethylformamide (DMF) were further selected for measurements of binary and ternary mixtures with a single sensor, as described in EXAMPLE 1. Using a single developed sensor, detection of individual vapors in their binary and ternary mixtures was demonstrated, as illustrated in FIG. 8. Correlation plots 50, 52 and 54, corresponding to chloroform, THF and DMF, respectively, between actual and predicted concentrations of the individual vapors in their mixtures, had excellent correlation coefficients. Vapors concentrations were from 0 to 0.15 P/Po where P is the partial pressure and Po is the saturated vapor pressure. These results demonstrated a unique ability of developed individual sensors to quantify 2-3 vapors in their mixtures. This discrimination has become possible because the sensor's multivariable response was modeled using the first, second, and third principal components (PCs) of the built PCA model.

Example 4

Selective Detection of Nine Vapors with a Single Sensor in the Presence of Variable Relative Humidity In this EXAMPLE, an RFID sensor (as described in EXAMPLE 1) coated with PEUT was also tested and a PCA evaluation demonstrated an RFID sensor capable of discriminating between up to nine vapors in the presence of variable relative humidity. Specifically, ethanol, 1-methoxy 2-propanol, methyl ethyl ketone, acetonitrile, toluene, choloroform, tetrahydrofuran (THF) dimethylformanmide (DMF) and acetone were selectively detected. In certain embodiments, the PCA analysis data may also be plotted in three dimensions, thereby providing an even greater ability to discriminate among various vapors.

Example 5

Selective Detection of Individual Nine Alcohols with a Single Sensor

Figure 9:
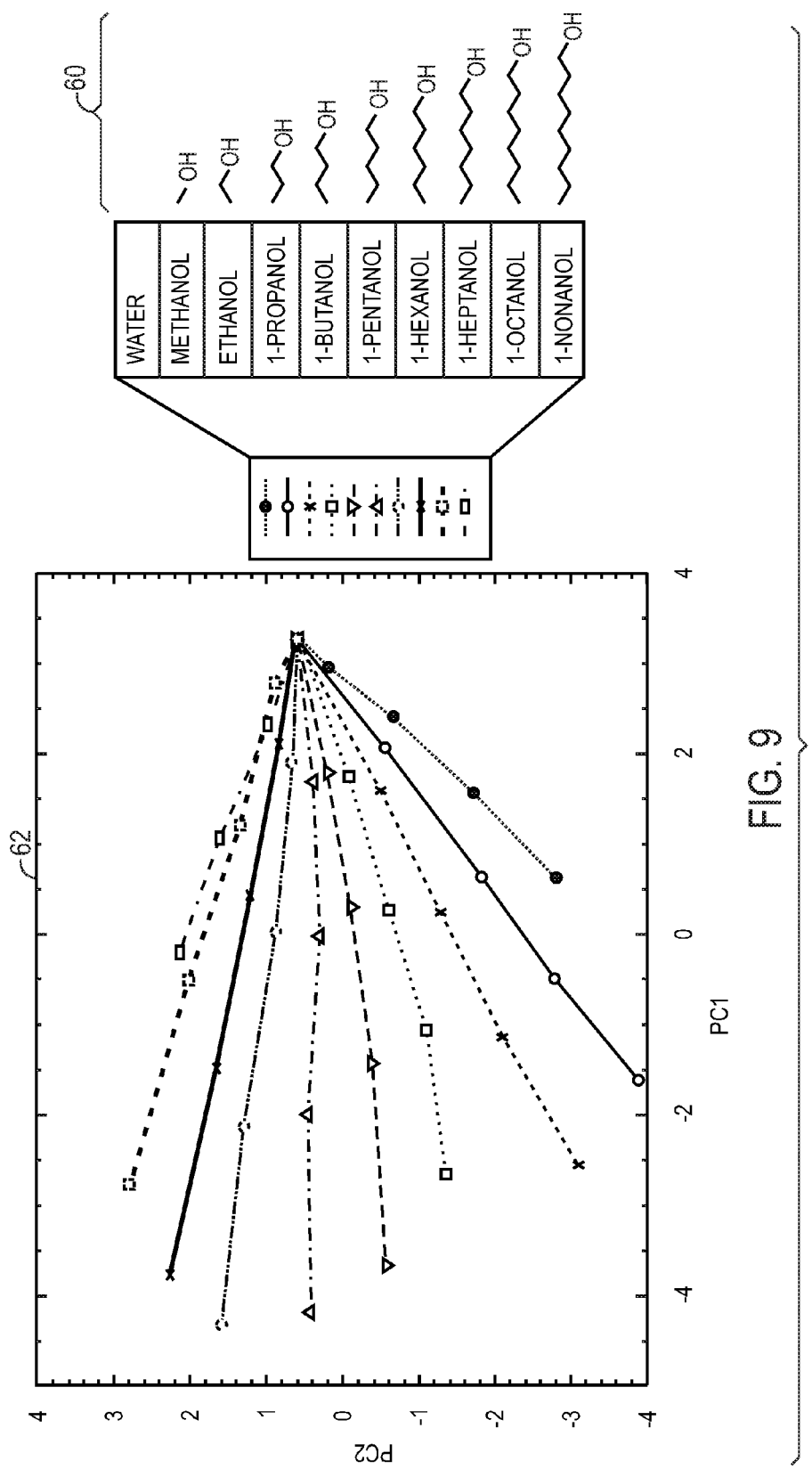
FIG. 9 illustrates test data demonstrating a single sensor capable of discriminating between water vapor and nine individual alcohol vapors from their homologous series, in accordance with embodiments of the invention.

With recognition of eight and nine diverse vapors demonstrated implementing sensors disclosed herein (EXAMPLEs 2 and 4, respectively), further testing was conducted to demonstrate selective detecting of individual, closely related vapors, such as alcohols from their homologous series and water vapor as an interferent. The tested sensing film made of octanethiol-capped Au nanoparticles was applied onto a sensor by drop casting. The structures of alcohols 60 are illustrated in FIG. 9. Results of selectivity evaluation of the sensor are also illustrated where a single sensor discriminates between water vapor and individual nine alcohol vapors from their homologous series, as shown by the PCA scores plot 62. Measurements were performed with concentrations of all vapors at 0, 0.089, 0.178, 0.267, and 0.356 $P/P_o$. No previous individual sensor has been reported to achieve this level of vapor discrimination, while this discrimination was achieved here with a single sensor.

Example 6

Rejection of 300,000-1,900,000-Fold Overloading from Water Vapor

Figure 10:
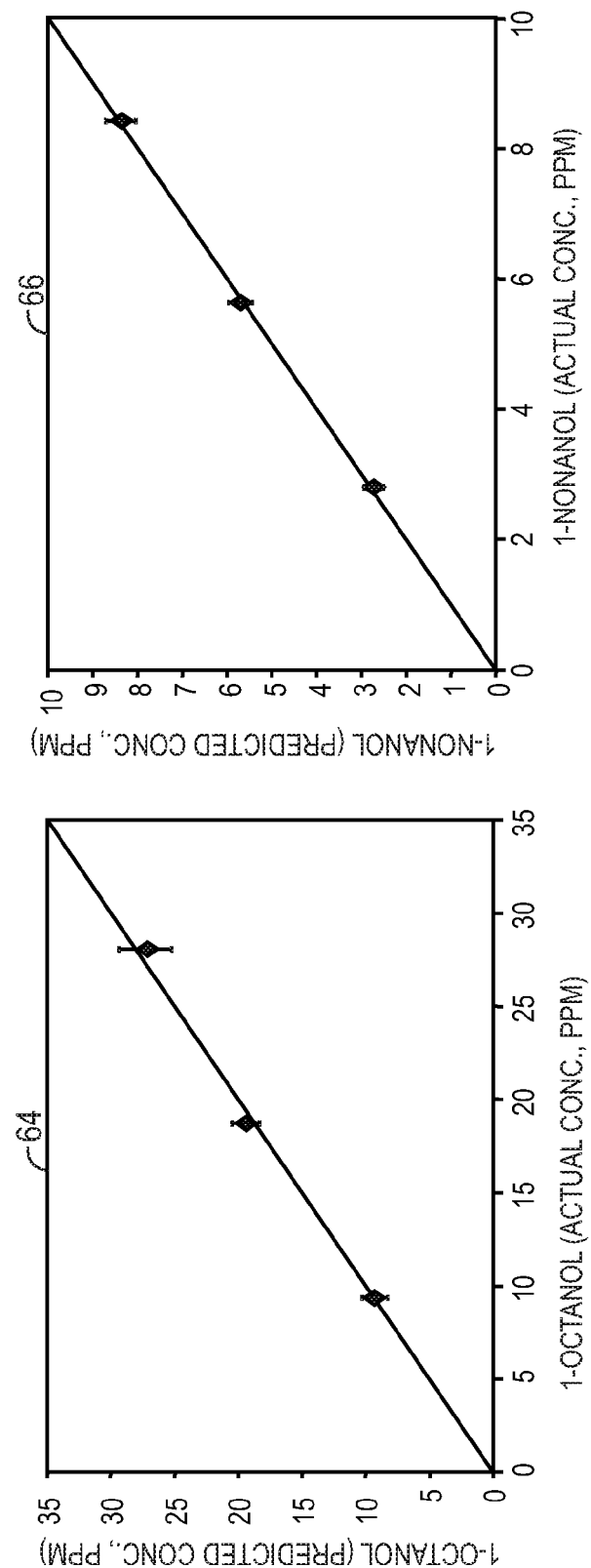
FIG. 10 illustrates comparative plots between the actual and predicted concentrations of 1-octanol and 1-nonanol, in accordance with embodiments of the invention.

The sensor described in EXAMPLE 5 was further tested for rejection of water vapor interference from measured multivariate sensor response of two polar model analytes (1-octanol and 1-nonanol). The sensor response to analyte vapors in mixtures with water vapor was corrected using multivariate analysis. FIG. 10 illustrates correlation plots 64 and 66 between the actual and predicted concentrations of 1-octanol (plot 64) and 1-nonanol (plot 66). Predicted concentrations of these vapors in the presence of different levels of humidity (ranging from 0 to 16,842 ppm) were calculated using multivariate analysis. The ratio of water vapor concentration to the detection limit concentration of the analyte in this mixture provided values of rejected water vapor overloading. The Tables of FIG. 11 summarize these findings for 1-octanol (Table 68) and 1-nonanol (Table 70). This data shows that a single sensor rejected up to 1,900,000-fold overloading from water vapor when measuring analyte vapors concentrations down to ppb levels.

Example 7

Highly Selective Multivariate Vapor Sensing

Figure 12:
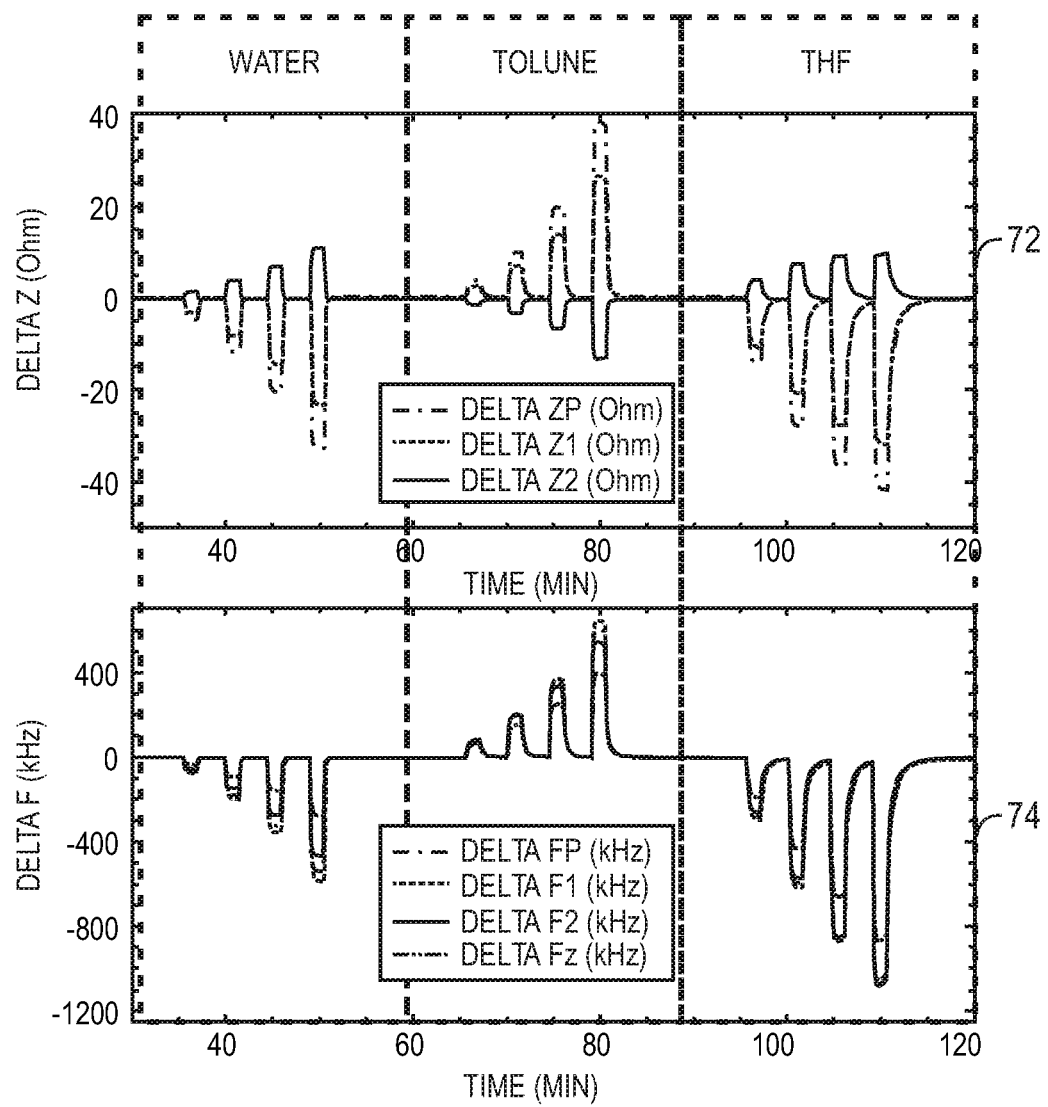
FIGS. 12-14 illustrate test data demonstrating a single sensor capable of highly selective multivariate vapor sensing, in accordance with embodiments of the invention.
Figure 13:
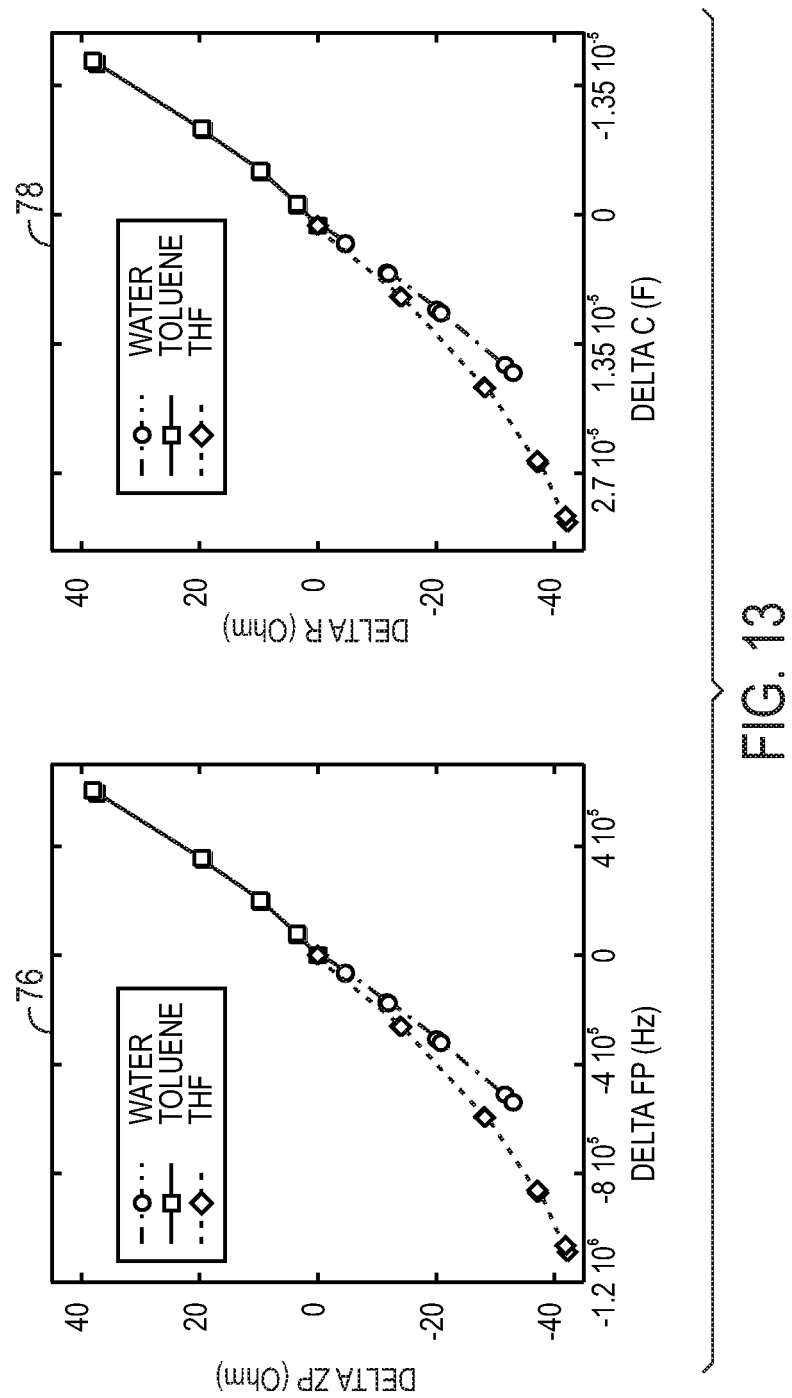
Figure 14:
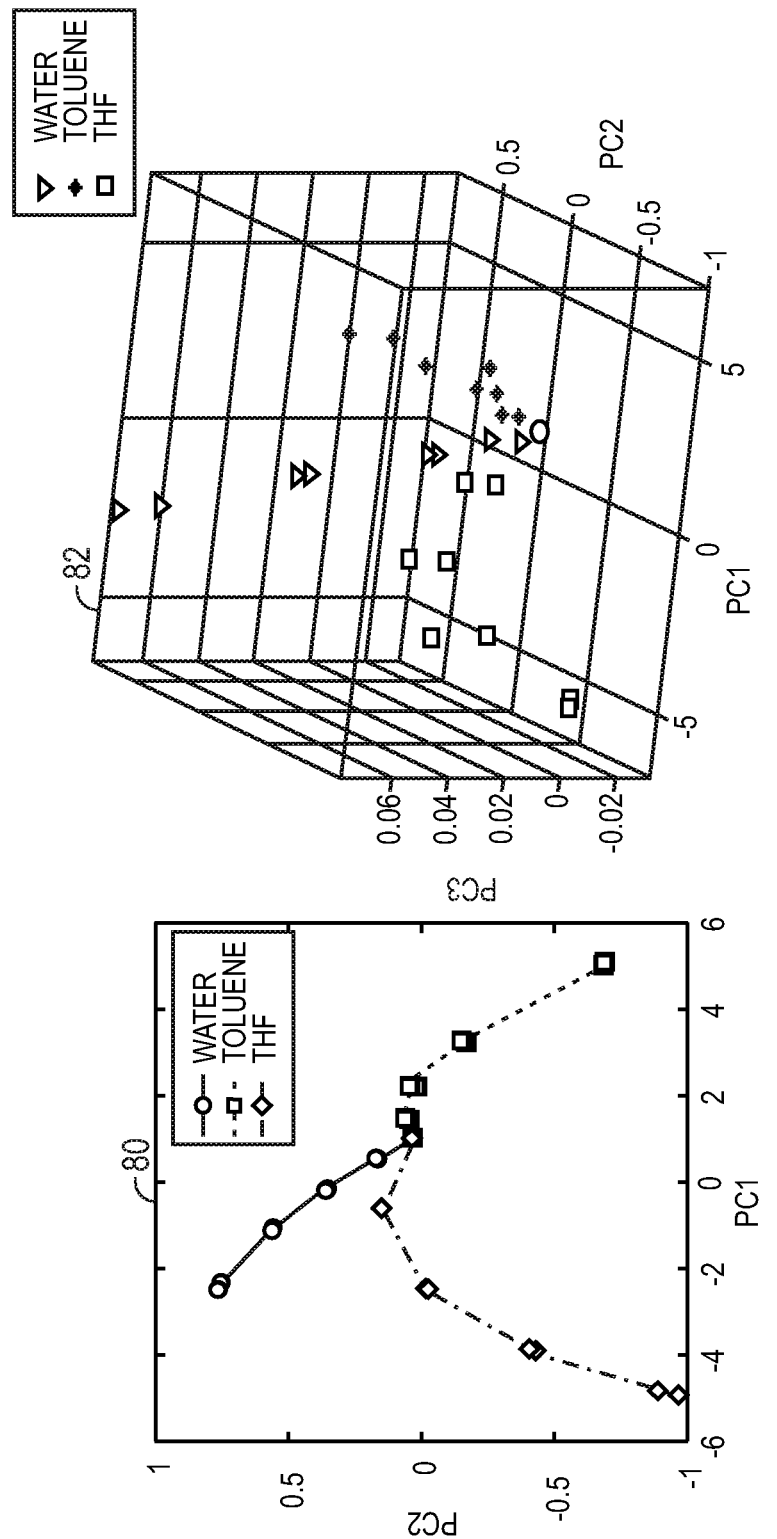

In another experiment, the sensing material used to coat the sensor was PEUT dissolved in a nonpolar solvent such as dichloromethane. During the experiment, the sensor was incrementally exposed to three vapors, water, toluene, and THF, over a period of time. Concentrations of each vapor were 0.18, 0.36, 0.53, and 0.71 P/Po. Dielectric constants of these analytes were 79 (water), 2.4 (toluene), and 7.5 (THF). As demonstrated and illustrated in FIGS. 12-14, a single passive sensor with multivariable response was able to easily discriminate between these three vapors. Specifically, the individual Fp, F1, F2, Fz, Zp, Z1 and Z2 responses, illustrated in plots 72 and 74 of FIG. 12, were analyzed using PCA tools. The relations between Fp and Zp are illustrated in plot 76 of FIG. 13, and the relations between calculated sensor resistance R and calculated sensor capacitance C are illustrated in plot 78. The plots 76 and 78 of FIG. 13 demonstrated a poor selectivity between water and THF vapors, as indicated by the closely positioned curves of water and THF responses. This poor selectivity between water and THF was because the dielectric constant of the polyetherurethane sensing film ($\varepsilon'_r$=4.8) is lower than water or THF but is higher than toluene. In contrast, the relationship between PC1 and PC2, illustrated in PCA scores plot 80 of FIG. 14, and the relationship between PC1, PC2, and PC3, illustrated in PCA scores plot 82 of FIG. 14, show a significant improvement in selectivity of sensor when data is analyzed using multivariate analysis tools. The responses for all three vapors are roughly pointing into three different directions in the 2D plot 80. Importantly, the responses PC1, PC2, and PC3 of plot 82 are in a 3D directional space demonstrating that the sensor performs as a multivariable device with three dimensions of response. Other sensors, for example, individual resistance and capacitance sensors produce only a single response per sensor. Even a combination of individual resistance and capacitance sensors produces only two responses per this combination, one response per sensor. Thus, a single multivariable response wireless sensor, in accordance with embodiments of the invention, reliably discriminated between these three example vapors using a "classic" polyetherurethane polymer.

Example 8

Figure 15:
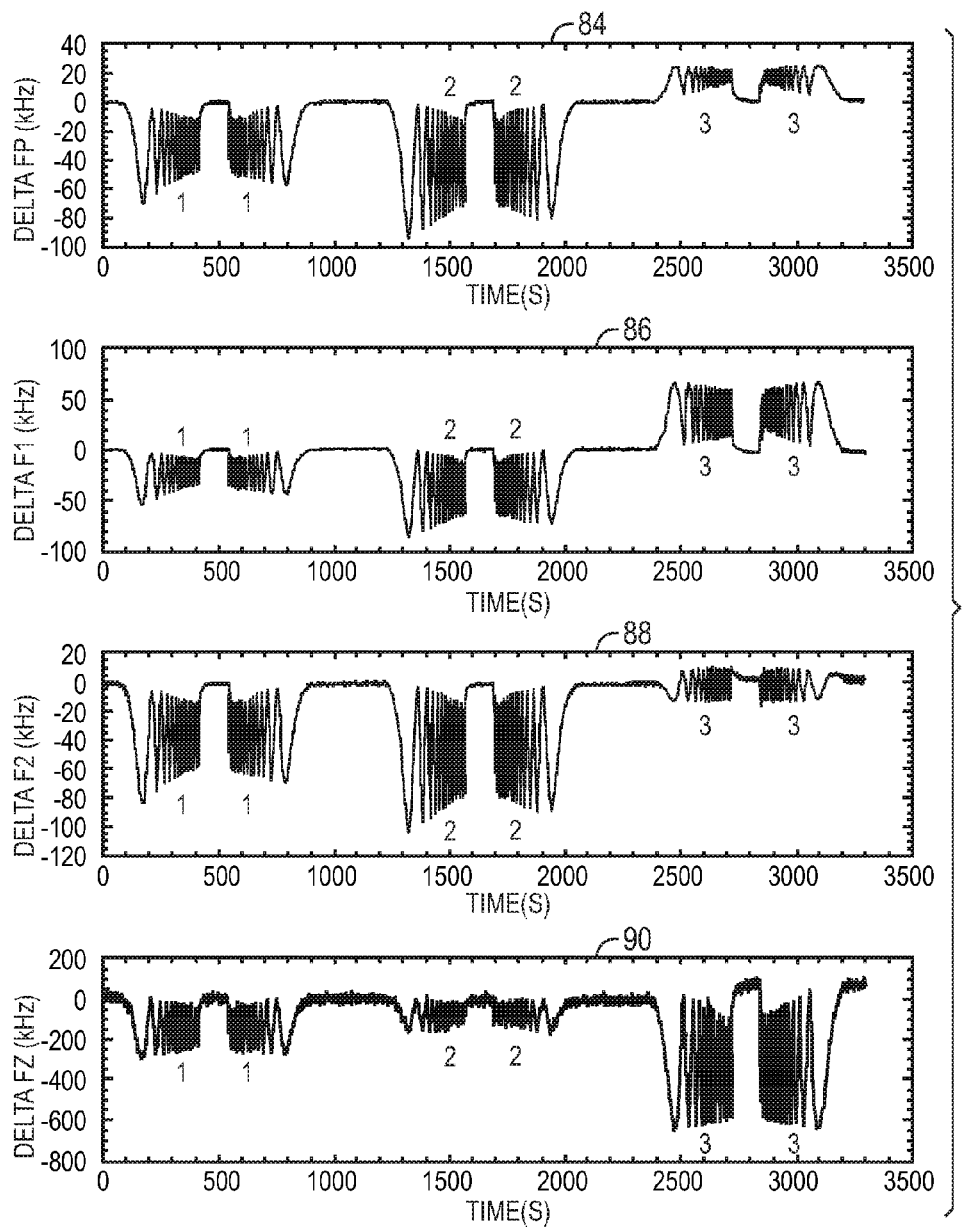
FIGS. 15-18 illustrate test data demonstrating independent contact resistance and contact capacitance responses, in accordance with embodiments of the invention.
Figure 16:
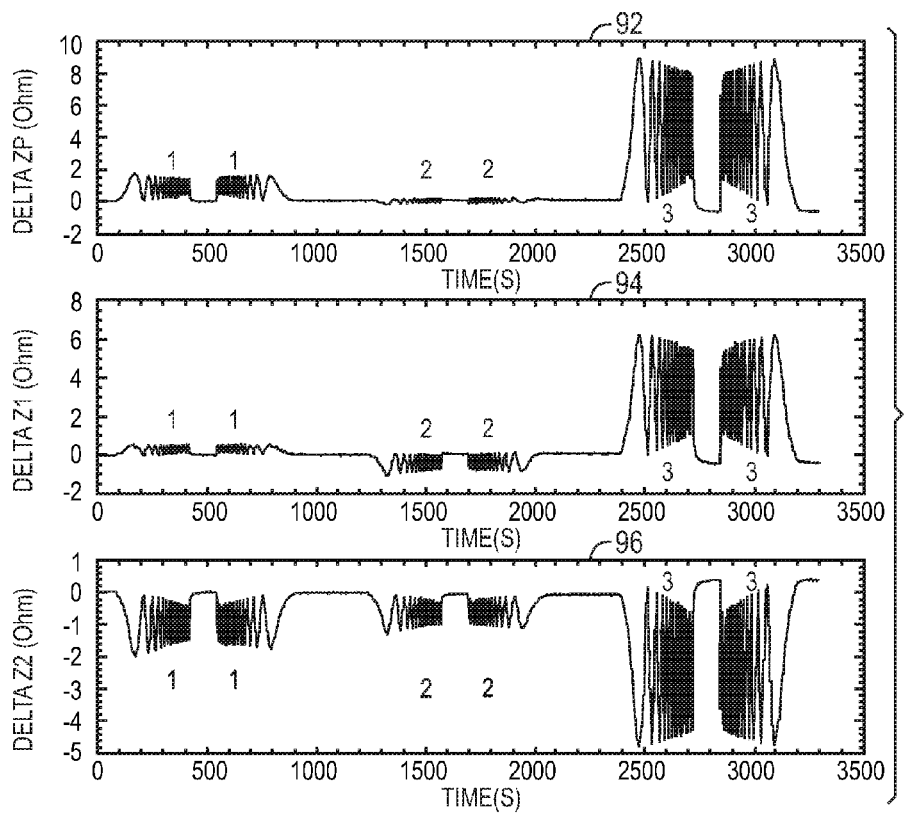

Demonstration of Independent Contact Resistance and Contact Capacitance Responses In another experiment, the sensing material used to coat the sensor was octanethiol-capped Au nanoparticles (Sigma Aldrich #6604426) mixed with zinc 1,4,8,11,15,18,22,25-octabutoxy-29H,31H-phthalocyanine (Sigma Aldrich #383813) applied onto a sensor by drop casting. During the experiment, the sensor was exposed to three vapors: acetone (vapor 1), acetonitrile (vapor 2), and toluene (vapor 3). Exposures were performed in a dynamic fashion where a vapor concentration was modulated with a sinusoidal function where its period was first reducing during the experiment and then increasing during the experiment. FIG. 15 illustrates Fp, F1, F2, and Fz dynamic responses to the three vapors, as indicated by plots 84, 86, 88 and 90, respectively. FIG. 16 illustrates Zp, Z1, and Z2 dynamic responses to the three vapors, as indicated by plots 92,94 and 96, respectively.

This experiment was performed to explore if contributions to the vapor responses arise from the same or from different portions of the transducer circuit. If the contributions to the vapor responses arise from the same portion of the transducer circuit, then dynamic responses related to frequency shifts Fp, F1, F2, and Fz should perfectly track each other and dynamic responses related to impedance change Zp, Z1, and Z2 should also perfectly track each other. However, if the contributions to the vapor responses are arising from different portions of the transducer circuit, then dynamic responses related to Fp, F1, F2, and Fz frequency shifts and dynamic responses related to impedance change Zp, Z1, and Z2 could be different. Furthermore, these differences can be present or absent depending on the nature of vapor because of the different types of interactions of different vapors with the sensing material and the material of the electrodes of the transducer.

The modulation of vapor concentration with a variable period provides the ability to evaluate the dynamics of the response to the vapor and the recovery from the vapor exposure. If the response of the sensing material to the vapor is faster than the smallest modulation period of the vapor concentration, then the amplitude of the sensor response will be unchanged with an increased speed of vapor concentration change. However, if the response of the sensing material to the vapor is slower than a predetermined modulation period of the vapor concentration, then the amplitude of the sensor response will start decreasing with an increased speed of vapor concentration change.

Similarly, if the recovery of the sensing material upon vapor exposure is faster than the smallest modulation period of the vapor concentration, then the amplitude of the sensor recovery will be unchanged with an increased speed of vapor concentration change. However, if the recovery of the sensing material upon vapor exposure is slower than the smallest modulation period of the vapor concentration, then the amplitude of the sensor recovery will start decreasing with an increased speed of vapor concentration change.

Thus, differences in the modulation of the amplitude of the sensor response and recovery should signify the existence of the contributions to the transducer performance that are arising from the different portions of the transducer circuit. These different portions of the transducer circuit can produce an additional diversity in sensor response and can provide the ability of the individual sensor to detect multiple vapors with high selectivity. This ability of the resonant transducer is completely different from a simple combination of individual resistance and capacitance sensors that produce only two responses per combination, one response per sensor.

Figure 17:
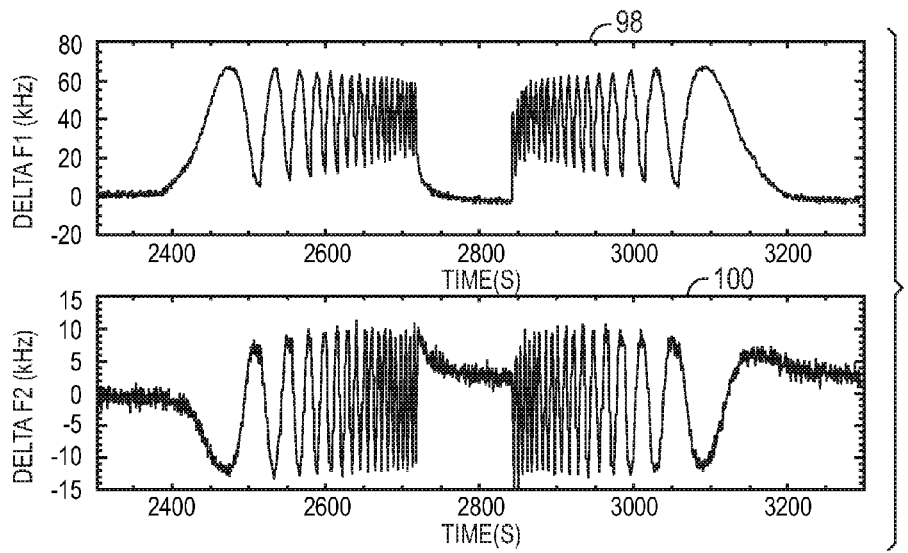
Figure 18:
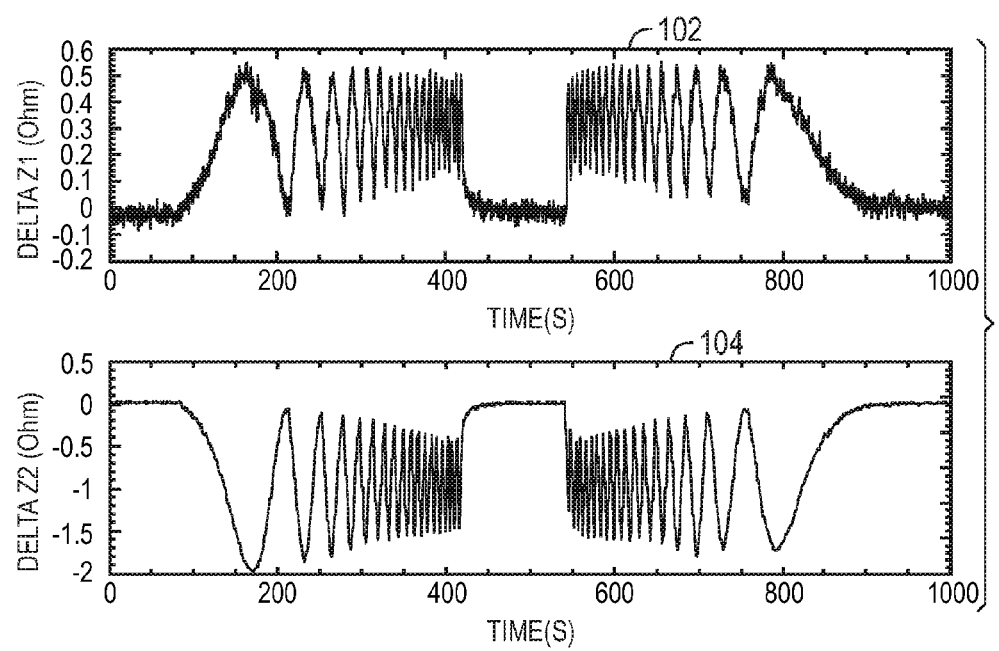

Referring to FIGS. 15-18, FIG. 15 illustrates Fp, F1, F2, and Fz dynamic responses to three vapors, and FIG. 16 illustrates Zp, Z1, and Z2 dynamic responses to three vapors such as acetone (vapor 1), acetonitrile (vapor 2), and toluene (vapor 3). The response and recovery amplitudes of vapors 1, 2, and 3 show diverse profiles. These diverse profiles are illustrated again in plots 98 and 100 of FIG. 17 for dynamic responses F1 and F2 to vapor 3 and in plots 102 and 104 for FIG. 18 for dynamic responses Z1 and Z2 to vapor 1. FIG. 17 demonstrates that vapor 3 affects different capacitance components of the transducer circuit (related to frequency changes in the LCR circuit) as evidenced by the differences in dynamic response and recovery profiles to vapor 3. FIG. 18 demonstrates that vapor 1 affects different resistance components of the transducer circuit (related to resistance changes in an LCR circuit) as evidenced by the differences in dynamic response and recovery profiles to vapor 1.

Example 9

Highly Sensitive Multivariate Vapor Sensing

While impedance spectroscopy is a classic technique to characterize fundamental materials properties, its well-accepted limitations in practical sensors for trace analyte detection include relatively low sensitivity and prohibitively long acquisition times over the broad frequency range. Thus, in order to enhance the ability to measure changes in properties of the sensing material, the sensing material was deposited onto the electrodes of the resonant LCR sensor circuit. Similarly, this placement of the electrodes enhanced the ability to measure changes in properties of the fluid in proximity to the electrodes of the resonant LCR sensor circuit.

Figure 19:
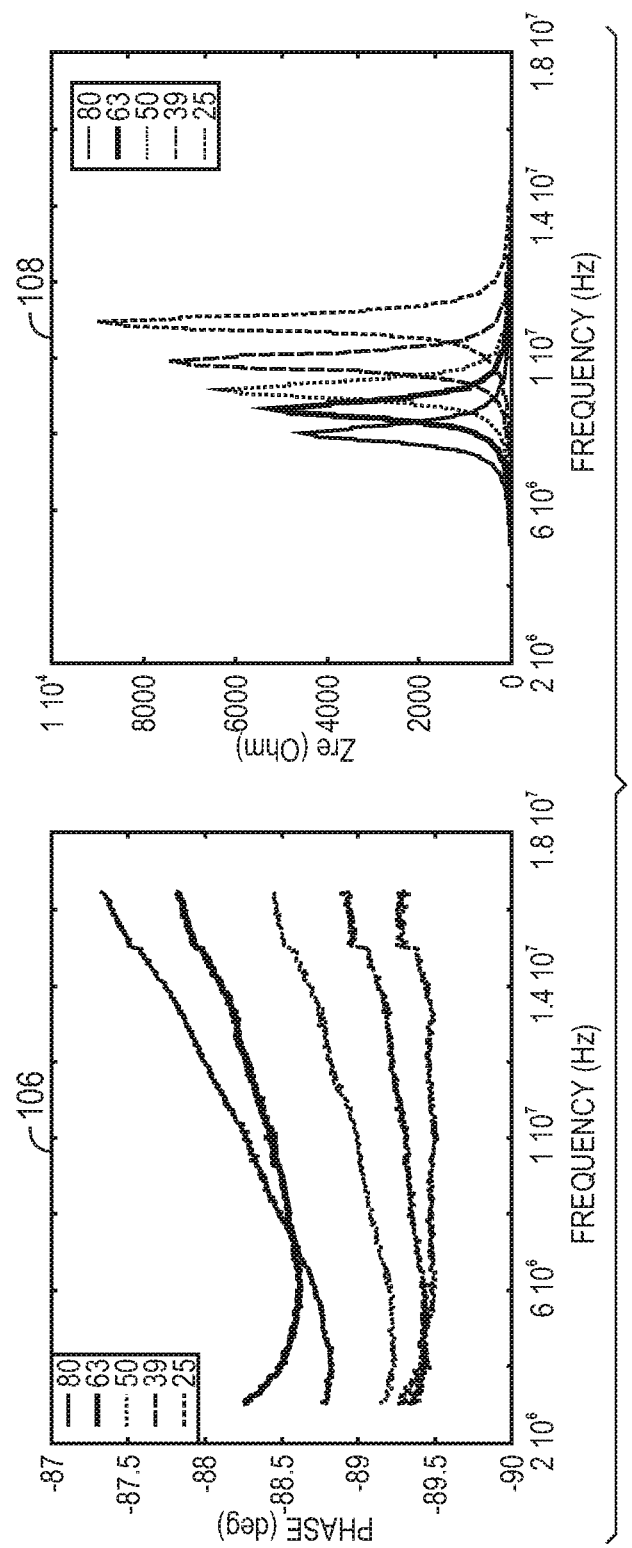
FIGS. 19-20 illustrates a comparison of conventional impedance spectroscopy and resonant sensing of embodiments having different dielectric constants.

In further experiments, effects of changing dielectric constant on sensing electrodes both with and without a resonator were tested. For example, fluids of five different dielectric constants (mixtures of water and ethanol at different ratios) were flowed into the cell and the impedance response of the sensor was monitored. The sensing ability of resonant sensors was compared with the sensing ability of resonant LCR sensors. In these comparisons, the signal-to-noise (SNR) and detection limit (DL) from two measurement configurations were determined. FIG. 19 illustrates results of validation experiments with solutions of $\in$=25-80 dielectric constants where results of phase shift measurements of an impedance spectrum and the peak shift of the resonance of the sensor were compared. Specifically, a comparison of conventional impedance spectroscopy and resonant sensing using solutions of different dielectric constants are illustrated in plots 106 and 108. Plot 106 illustrates the sensor response (phase shift) measured using conventional impedance spectroscopy. Plot 108 illustrates the sensor response (frequency shift) measured using a resonance sensor structure. Five different dielectric constants $\in$ ranging from 25 to 80 were produced using solutions with different water/ethanol ratios, as illustrated in plots 106 and 108.

Figure 20:
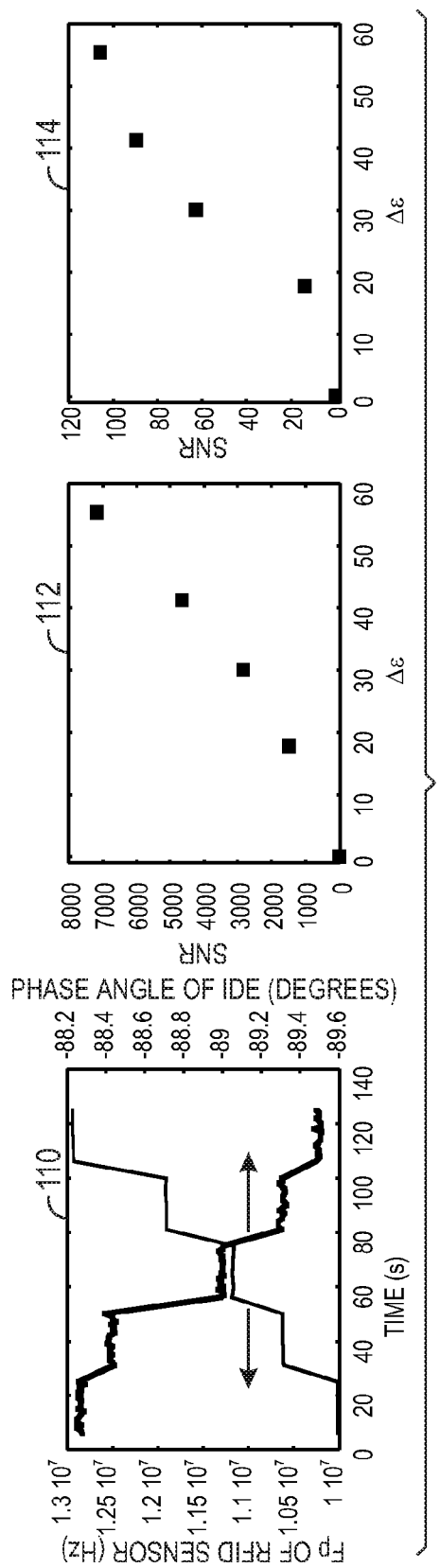

From the analysis of the collected data, it was observed that conventional impedance spectroscopy measurements have a much larger relative noise in the signal, as illustrated by plot 110 of FIG. 20. To evaluate the SNR of sensor response, data was processed, as shown in plots 112 (frequency shift response of the LCR sensor) and 114 (phase shift response of conventional impedance spectroscopy sensor) of FIG. 20. Compared to the conventional impedance spectroscopy (plot 114), the resonant LCR sensor (plot 112) provided an at least 100-fold enhancement in the SNR over the smallest measured range of $\Delta\in$ with the corresponding improvement of detection limit of dielectric constant determinations.

Example 10

Improvement of Selectivity of Sensing of Vapors of Same Dielectric Constant Using Power Modulation Embodiments of the invention also provide the ability to discriminate between vapors of similar dielectric constant at room temperature, as illustrated in the experimental data of FIGS. 21-25. The selected vapors for this experiment were 1-pentanol (vapor 1), paraldehyde (vapor 2), and salicylaldehyde (vapor 3). The discrimination was achieved using power modulation. An interdigital chip served as a complementary sensor that was attached across an antenna of a passive RFID tag. The chip was 2×2 mm$^2$ and had gold electrodes that were 10 μm wide and 10 μm spaced from each other. A sensing film made of octanethiol-capped Au nanoparticles, manufactured by Sigma-Aldrich®, product #660426, was applied onto a sensor chip by drop casting. The power of operation of the RFID sensor was controlled from −10 dBm to 0 dBm.

Figure 21:
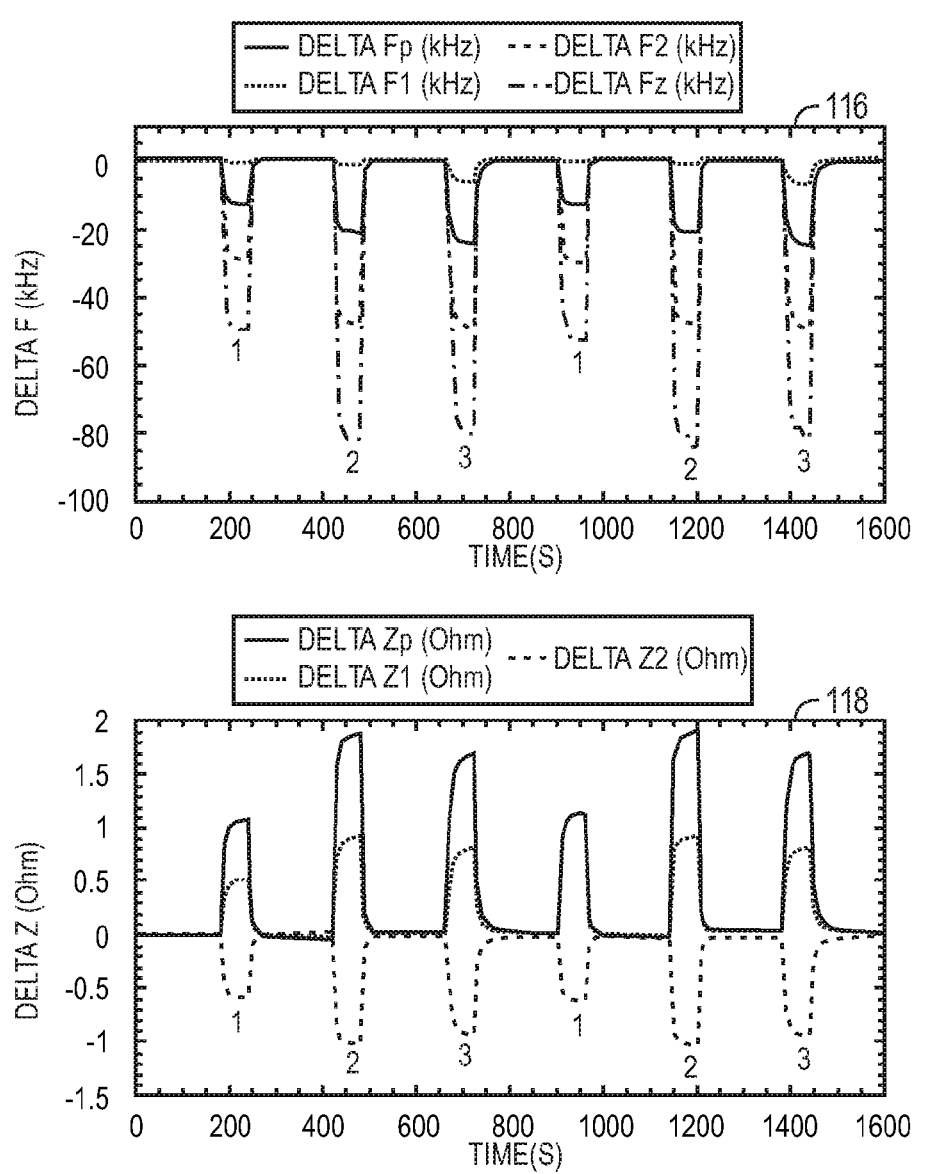
FIGS. 21-25 illustrate test data demonstrating improved selectivity of sensing of vapors of the same dielectric constant using power modulation.
Figure 22:
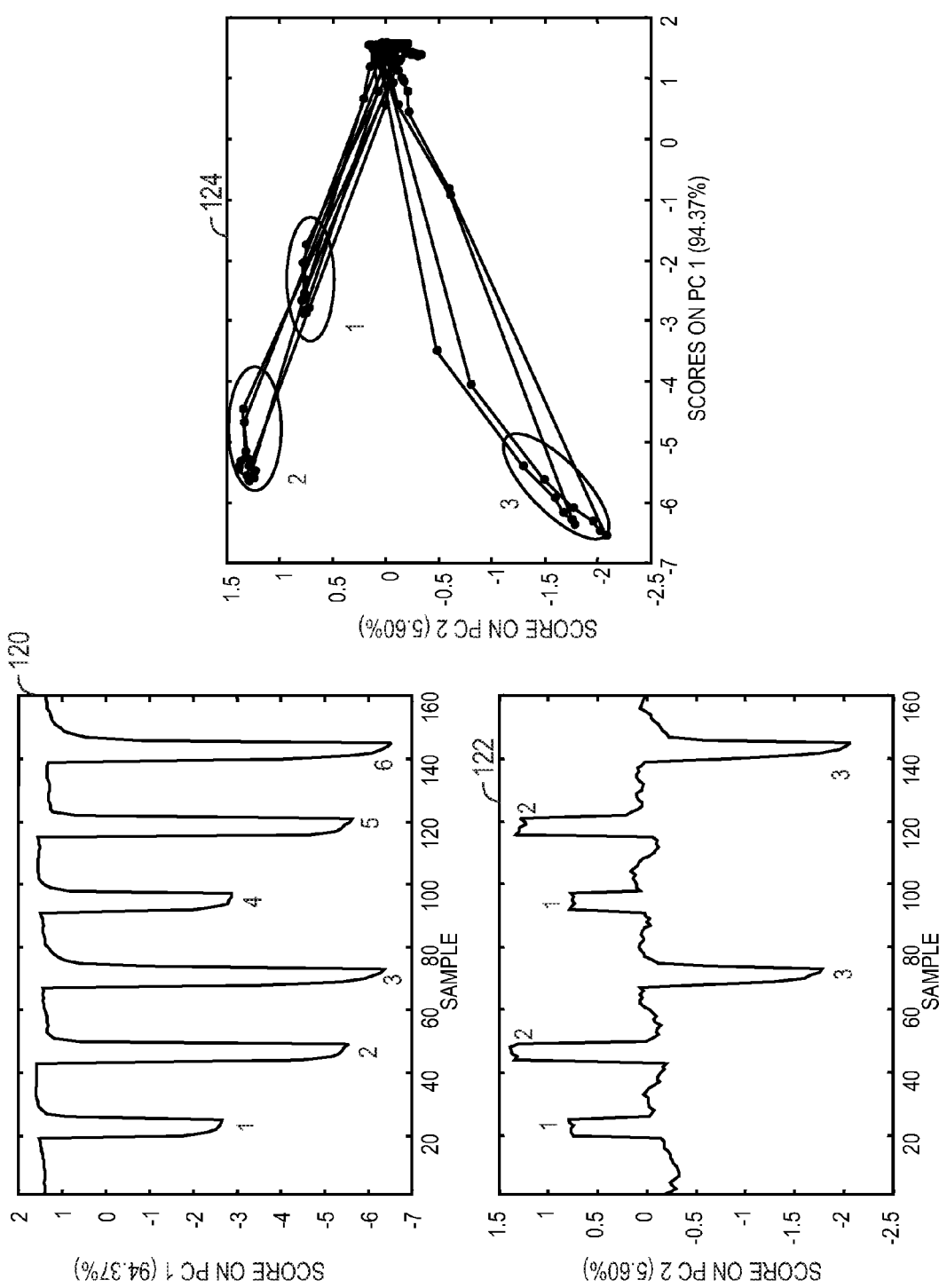

Plots 116 and 118 of FIG. 21 illustrate individual Fp, F1, F2, Fz, Zp, Z1 and Z2 responses upon a −10 dBm excitation. Results of PCA analysis of these responses is illustrated in FIG. 22. Plots 120 and 122 show the first two principal components as a function of measurement time. Plot 124 shows the first two principal components demonstrating the difficulties in discriminating between vapors 1 and 2.

Figure 23:
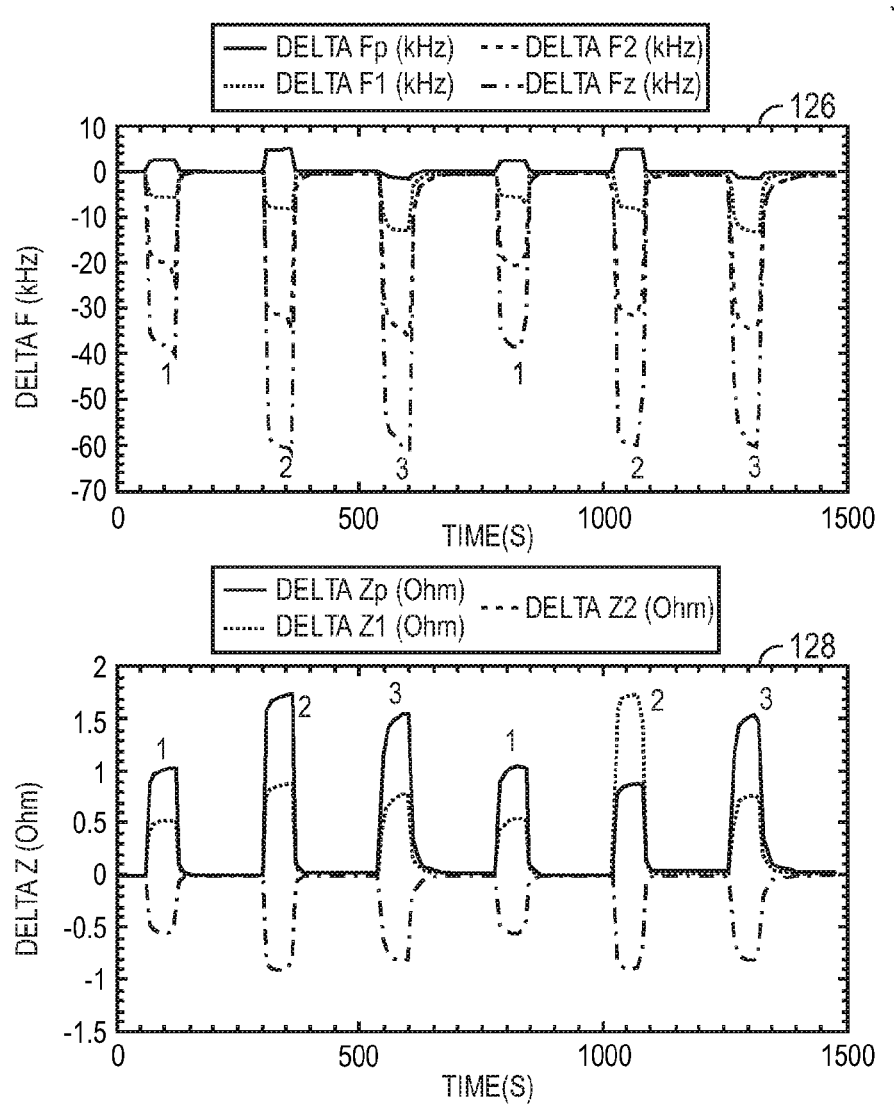
Figure 24:
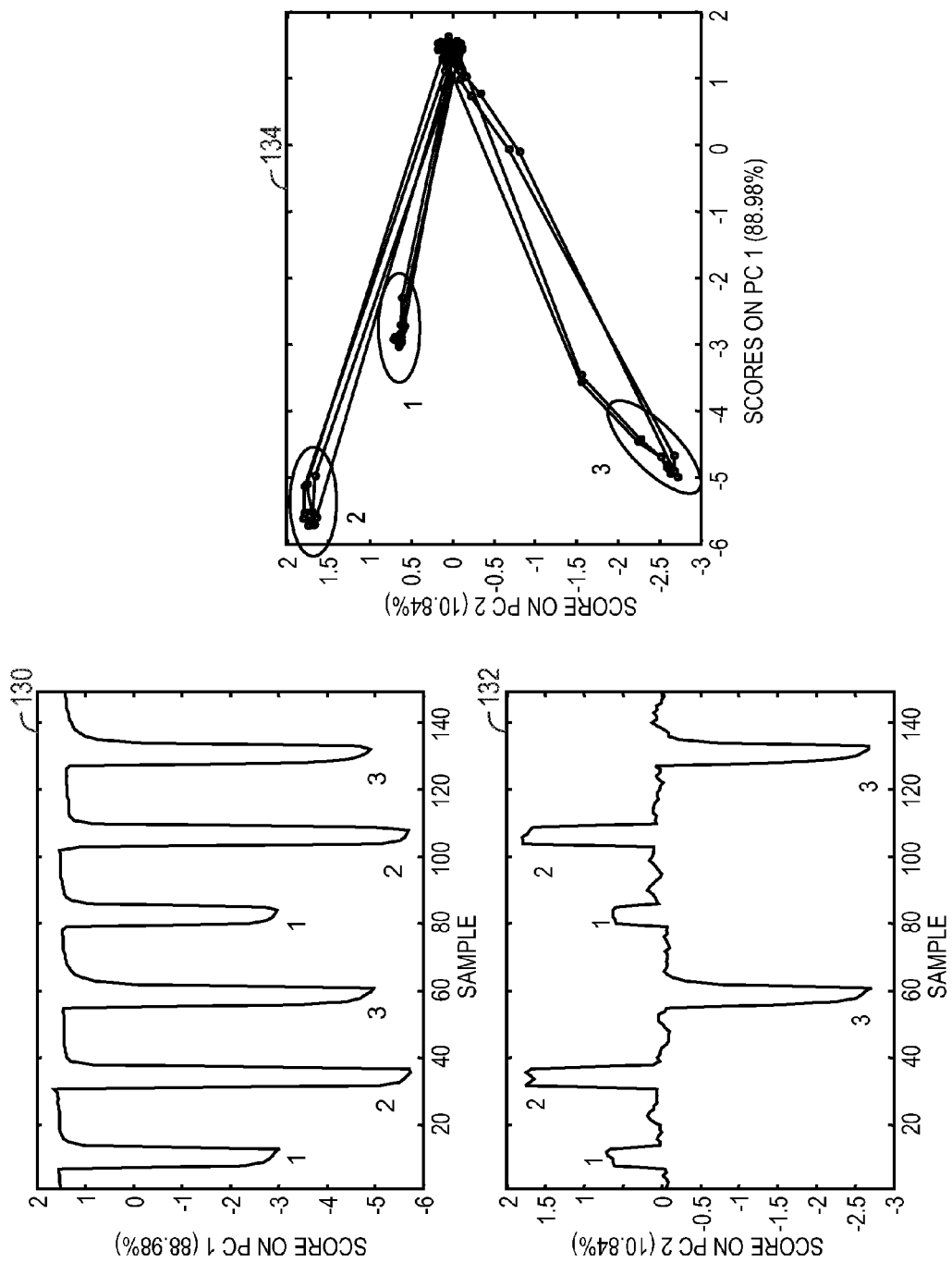

Plots 126 and 128 of FIG. 23 illustrate individual Fp, F1, F2, Fz, Zp, Z1 and Z2 responses upon a 0 dBm excitation. Results of PCA analysis of these responses is illustrated in FIG. 24. Plots 130 and 132 show of the first two principal components as a function of measurement time. Plot 134 shows the first two principal components demonstrating the discrimination between vapors 1, 2, and 3.

Figure 25:
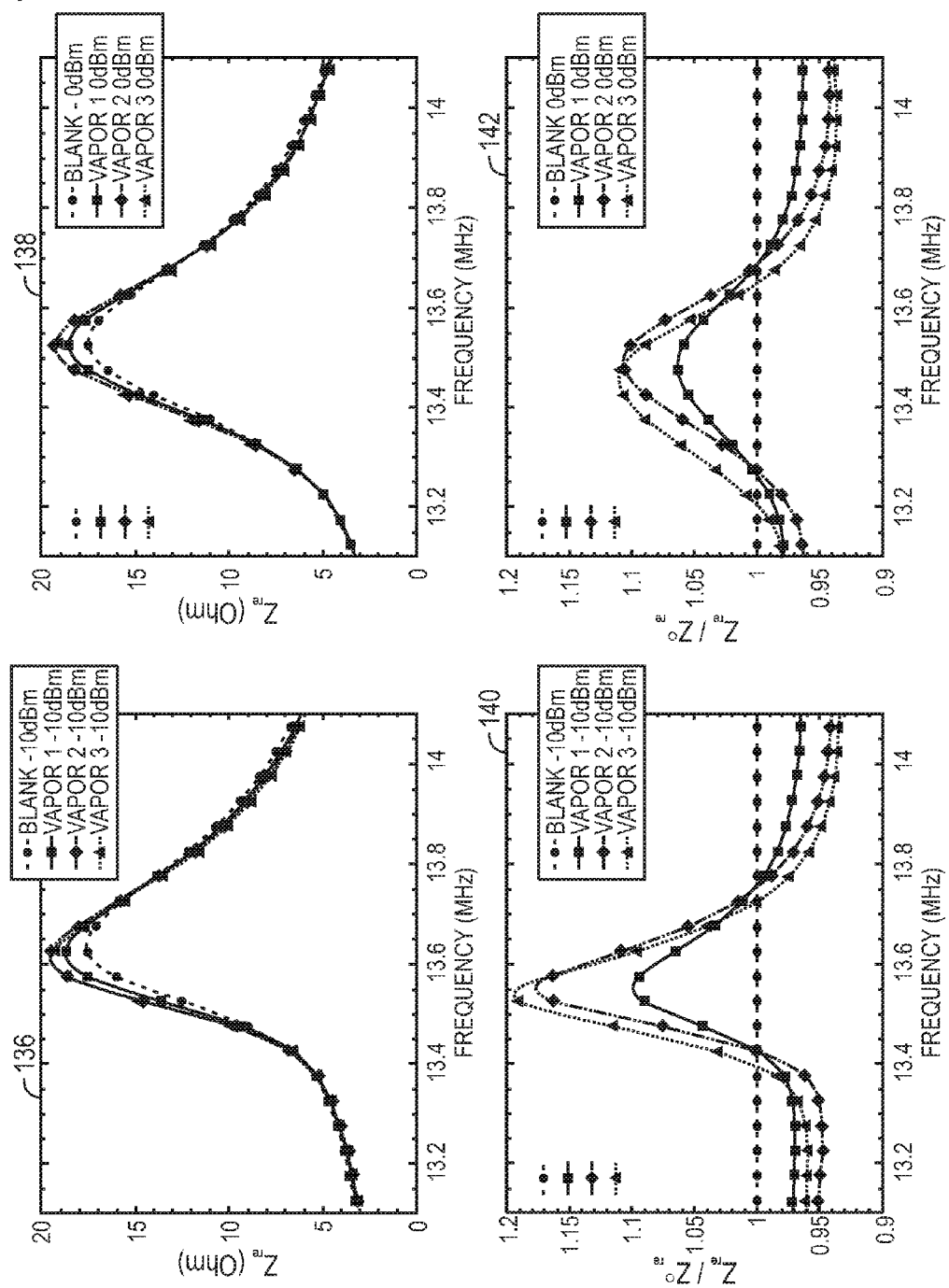

FIG. 25 illustrates examples of changes of the resonance impedance spectral profiles of the passive RFID sensor upon −10 and 0 dBm excitation when the sensor was exposed to a blank gas without tested vapors and to vapors 1, 2, and 3. Plots 136 and 138 of FIG. 25 illustrate the changes in the real part of the resonance impedance spectra $Z_{re}(f)$ at −10 and 0 dBm excitation, respectively. To illustrate the details of the spectral changes, the spectra of sensor response to vapors 1, 2, and 3 were normalized by the relevant spectra $Z°_{re}(f)$ of the sensor exposed to a blank gas without tested vapors. Plots 140 and 142 illustrate these normalized spectra $Z_{re}/Z°_{re}$ at −10 and 0 dBm excitation, respectively. Plots 140 and 142 conclusively demonstrate that the vapor-induced resonance impedance is significantly changed upon changes in the excitation power from −10 dBm to 0 dBm. These changes provide the ability to discriminate between all three vapors at an appropriately selected level of excitation power for the RFID sensor as shown in plot 134 of FIG. 24.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensor, comprising:
a single resonant inductor-capacitor-resistor (LCR) circuit; and
a sensing material disposed over at least a portion of the single LCR circuit, wherein the sensing material is configured to allow selective detection of at least six different analyte fluids from an analyzed fluid mixture.

2. The sensor, as set forth in claim 1, comprising a memory chip.

3. The sensor, as set forth in claim 1, wherein the sensor comprises an RFID sensor.

4. The sensor, as set forth in claim 1, comprising a coil.

5. The sensor, as set forth in claim 1, wherein the sensing material is disposed between electrodes of the single LCR circuit.

6. The sensor, as set forth in claim 1, wherein the sensing material comprises a dielectric polymer.

7. The sensor, as set forth in claim 1, wherein the sensing material comprises synthetic dielectric polymers, synthetic conducting polymers, polymer formulations, biomolecules, cavitands, monolayer-protected metal nanoparticles, metal nanoparticle cores with organic ligand shells, porphyrins, phthalocyanines, and their combinations.

8. The sensor, as set forth in claim 1, wherein the sensing material comprises composite sensing material comprising a plurality of individual sensing materials that are homogeneously or inhomogeneously mixed or locally patterned over specific portions of the single LCR circuit resonator such that each of the plurality of individual sensing materials is arranged to respond to analytes by predominantly different response mechanisms.

9. The sensor, as set forth in claim 8, wherein the composite sensing material phase-separate due to hydrophylic/hydrophobic interactions, mutual immiscibility, or formed as sectors of individual materials deposited adjacent to each other onto a single sensor, or as formed as layers of individual materials deposited on top of each other onto a single sensor.

10. The sensor, as set forth in claim 1, wherein the sensor is configured to sense a first fluid in the analyzed fluid in the presence of a second fluid in the analyzed fluid, wherein a concentration of the second fluid is at least ten times greater than a concentration of the first fluid.

11. The sensor, as set forth in claim 10, wherein the second fluid is water vapor.

12. The sensor, as set forth in claim 1, wherein the sensor is configured to sense a first fluid in the analyzed fluid in the presence of a second fluid in the analyzed fluid, wherein a concentration of the second fluid is at least 1 million times greater than a concentration of the first fluid.

13. The sensor, as set forth in claim 1, wherein the sensor is configured as a single-use sensor.

14. The sensor, as set forth in claim 1, wherein the sensor is a wireless sensor.

15. The sensor, as set forth in claim 1, wherein the sensor is configured as a single-use sensor.

16. The sensor, as set forth in claim 1, wherein the sensor is a wireless sensor.

17. A sensor, comprising:
a resonant inductor-capacitor-resistor (LCR) circuit; and
a sensing material disposed over at least a portion of the LCR circuit, wherein the sensing material is configured to allow selective detection of at least six different analyte fluids from an analyzed fluid mixture, wherein the sensing material comprises composite sensing material comprising a plurality of individual sensing materials that are homogeneously or inhomogeneously mixed or locally patterned over specific portions of the LCR circuit such that each of the plurality of individual sensing materials is arranged to respond to analytes by predominantly different response mechanisms, and wherein the composite sensing material phase-separate due to hydrophylic/hydrophobic interactions, mutual immiscibility, or formed as sectors of individual materials deposited adjacent to each other onto a single sensor, or as formed as layers of individual materials deposited on top of each other onto a single sensor.

18. The sensor, as set forth in claim 17, wherein the LCR circuit comprises a single LCR circuit.

19. The sensor, as set forth in claim 17, wherein the sensor is configured to sense a first fluid in the analyzed fluid in the presence of a second fluid in the analyzed fluid, and wherein a concentration of the second fluid is at least 1 million times greater than a concentration of the first fluid.

20. The sensor, as set forth in claim 17, comprising a memory chip.

21. The sensor, as set forth in claim 17, wherein the sensor comprises an RFID sensor.

22. The sensor, as set forth in claim 17, comprising a coil.

23. The sensor, as set forth in claim 17, wherein the sensing material is disposed between electrodes of the LCR circuit.

24. The sensor, as set forth in claim 17, wherein the sensing material comprises a dielectric polymer.

25. The sensor, as set forth in claim 17, wherein the sensing material comprises synthetic dielectric polymers, synthetic conducting polymers, polymer formulations, biomolecules, cavitands, monolayer-protected metal nanoparticles, metal nanoparticle cores with organic ligand shells, porphyrins, phthalocyanines, and their combinations.

26. The sensor, as set forth in claim 17, wherein the sensor is configured to sense a first fluid in the analyzed fluid in the presence of a second fluid in the analyzed fluid, wherein a concentration of the second fluid is at least ten times greater than a concentration of the first fluid.

27. The sensor, as set forth in claim 26, wherein the second fluid is water vapor.

28. The sensor, as set forth in claim 17, wherein the sensor is configured as a single-use sensor.

29. The sensor, as set forth in claim 17, wherein the sensor is a wireless sensor.

30. A sensor, comprising:
a resonant inductor-capacitor-resistor (LCR) circuit; and
a sensing material disposed over at least a portion of the LCR circuit, wherein the sensing material is configured to allow selective detection of at least six different analyte fluids from an analyzed fluid mixture, wherein the sensor is configured to sense a first fluid in the analyzed fluid in the presence of a second fluid in the analyzed fluid, and wherein a concentration of the second fluid is at least 1 million times greater than a concentration of the first fluid.

31. The sensor, as set forth in claim 30, wherein the LCR circuit comprises a single LCR circuit.

32. The sensor, as set forth in claim 30, wherein the sensing material comprises composite sensing material comprising a plurality of individual sensing materials that are homogeneously or inhomogeneously mixed or locally patterned over specific portions of the LCR circuit such that each of the plurality of individual sensing materials is arranged to respond to analytes by predominantly different response mechanisms.

33. The sensor, as set forth in claim 32, wherein the composite sensing material phase-separate due to hydrophylic/hydrophobic interactions, mutual immiscibility, or formed as sectors of individual materials deposited adjacent to each other onto a single sensor, or as formed as layers of individual materials deposited on top of each other onto a single sensor.

34. The sensor, as set forth in claim 30, comprising a memory chip.

35. The sensor, as set forth in claim 30, wherein the sensor comprises an RFID sensor.

36. The sensor, as set forth in claim 30, comprising a coil.

37. The sensor, as set forth in claim 30, wherein the sensing material is disposed between electrodes of the LCR circuit.

38. The sensor, as set forth in claim 30, wherein the sensing material comprises a dielectric polymer.

39. The sensor, as set forth in claim 30, wherein the sensing material comprises synthetic dielectric polymers, synthetic conducting polymers, polymer formulations, biomolecules, cavitands, monolayer-protected metal nanoparticles, metal nanoparticle cores with organic ligand shells, porphyrins, phthalocyanines, and their combinations.

40. The sensor, as set forth in claim 30, wherein the second fluid is water vapor.

* * * * *